(12) United States Patent
Wheeler

(10) Patent No.: US 6,670,332 B1
(45) Date of Patent: Dec. 30, 2003

(54) COMPLEX CATIONIC LIPIDS HAVING QUARTERNARY NITROGENS THEREIN

(75) Inventor: Carl J. Wheeler, Poway, CA (US)

(73) Assignee: Vical Incorporated, San Diego, CA (US)

( * ) Notice: Subject to any disclaimer, the term of this patent is extended or adjusted under 35 U.S.C. 154(b) by 0 days.

(21) Appl. No.: 09/092,486

(22) Filed: Jun. 5, 1998

Related U.S. Application Data

(63) Continuation-in-part of application No. 08/565,756, filed on Nov. 30, 1995, now abandoned.

(51) Int. Cl.$^7$ ............................................... A01N 43/04
(52) U.S. Cl. ............................. 514/44; 435/6; 436/501; 514/1; 514/2; 530/300; 530/350; 536/22.1
(58) Field of Search ............................. 435/6; 436/501; 514/44, 1, 2; 236/22.1, 23.1, 24.1, 24.3–24.33; 937/77, 78; 530/300, 350

(56) References Cited

U.S. PATENT DOCUMENTS

| | | | | |
|---|---|---|---|---|
| 2,368,208 A | 1/1945 | Epstein | ..................... | 260/404.5 |
| 3,265,719 A | 8/1966 | Cowen et al. | .............. | 260/404 |
| 4,864,060 A | 9/1989 | Karalis et al. | .............. | 564/292 |
| 5,049,386 A | 9/1991 | Eppstein et al. | ............ | 424/427 |
| 5,068,431 A | 11/1991 | Karalis et al. | .............. | 564/301 |
| 5,144,060 A | 9/1992 | Morita et al. | ................ | 560/170 |
| 5,264,618 A | 11/1993 | Felgner et al. | .............. | 560/224 |
| 5,279,833 A | 1/1994 | Rose | ......................... | 424/450 |
| 5,334,761 A | 8/1994 | Gebeyehu et al. | .......... | 564/197 |
| 5,869,715 A | * 2/1999 | Nantz et al. | ................. | 554/110 |
| 6,075,012 A | * 6/2000 | Gebeyehu et al. | ............ | 514/44 |

FOREIGN PATENT DOCUMENTS

| | | |
|---|---|---|
| EP | 747351 | 12/1996 |
| JP | 3258900 | 11/1991 |
| WO | 9117424 | 11/1991 |
| WO | WO 94/05624 | 3/1994 |
| WO | PCT/US94/13362 | 11/1994 |
| WO | PCT/US94/13428 | 11/1994 |
| WO | WO 96/22379 | 7/1996 |
| WO | WO 96/40961 | 12/1996 |

OTHER PUBLICATIONS

G. Nabel, et al., "Immunotherapy of Malignancy by In Vivo Gene Transfer in Tumors", Human Gene Therapy, 3:399–410, (1992).

A. Rosenthal, et al., "A Synthetic Inhibitor of Venom Lecithinase A*", The Journal of Biological Chemistry, 235(8), (1960).

P. Felgner, et al. "Lipofection: A highly efficient, lipid–medicated NDA–transfection procedure", Biochemistry, 84:7413–7417, (1987).

J. Felgner, et al., "Enhanced Gene Delivery and Mechansim Studies with a Novel Series of Cationic Lipid Formulations*", The Journal of Biological Chemistry, 269:2550–2561, (1994).

Wheeler, C.J., et al., "Converting an alcohol to an amine in a cationic lipid dramatically alters the co–lipid requirement, cellular transfection activity and the ultrastructure of DNA–cytofectin complexes", Biochimica et Biophysica Acta 1280:1–11 (1996).

Solodin, et al., SYNLETT, "Synthesis of Novel Cationic Lipids with a Guanidine Group. Cationic Lipids $3^1$", pp. 617–18, Jul. 1996.

Solodin, et al., SYNLETT, "Synthesis of Amphiphilic Piperdinium Derivatives. Cationic Lipids $4^1$", p. 619, Jul. 1996.

Solodin, et al., SYNLETT, "Synthesis of Amphiphilic Derivatives of N–Methyldiethanolamine. Cationic Lipids $5^1$", p. 620, Jul. 1996.

* cited by examiner

*Primary Examiner*—Ardin H. Marschel
(74) *Attorney, Agent, or Firm*—Sterne, Kessler, Goldstein & Fox P.L.L.C.

(57) ABSTRACT

Cationic lipids having a derivatized quaternary ammonium head group that provide improved cell targeting ability and enhanced transfective efficacy for introducing molecules into cells are provided.

27 Claims, 7 Drawing Sheets

COMPLEX CATIONIC LIPIDS HAVING QUARTERNARY NITROGENS THEREIN

RELATED APPLICATIONS

The present application is a continuation-in-part of U.S. patent application Ser. No. 08/565,756, filed Nov. 30, 1995, now abandoned, the disclosure of which is incorporated by reference in its entirety.

The present invention relates to cytofectins comprising complex amphiphilic lipids in which a bioactive agent which is recognized by biological systems is joined to a Rosenthal Inhibitor core structure through an alkyl linking group. A number of alkyl linking groups are disclosed, including carboxy, carbamyl, ureyl, thioureyl, and guanidyl cytofectins.

A second aspect of the present invention relates to such cytofectins having a primary amine within 8 carbons of the quaternary nitrogen.

A third aspect of the present invention relates to such cytofectins wherein the biologically active moiety is an amino acid or peptide selected from those moieties which are non-polar, polar and uncharged, and negatively charged at physiological pH.

A fourth aspect of the present invention relates to such cytofectins wherein the biologically active moiety contains alternative amino acids which are not generally found in natural organisms.

A fifth aspect of the present invention relates to disubstituted RI cytofectins having two heterosubstituted groups on the quaternary nitrogen.

A sixth aspect of the present invention relates to ether cytofectins.

BACKGROUND OF THE INVENTION

Cationic lipids are amphiphilic molecules having a lipophilic region, commonly comprising one or more hydrocarbon or alkyl groups, and a hydrophilic region comprising at least one positively charged polar head group. Cationic lipids are useful for facilitating the transport of macromolecules through the plasma membrane of cells and into the cytoplasm by forming net positively charged complexes. The process, which can be carried out in vivo as well as in vitro, is known as transfection, and the cationic lipids used in such techniques are known as cytofectins.

Cytofectins which enhance transfection efficiency as little as 3 fold over that observed with naked DNA are beneficial, although preferably transfection efficiency is increased 5–10 fold, and more preferably transfection efficiency is enhanced more than 10 fold.

Typically, cytofectins are combined with a neutral zwitterionic lipid such as a phospholipid, because it has been found that the two amphiphilic lipid species in combination are able to form vesicles comprising ordered lipid bilayers that are more effective at transfection than the cytofectin alone. These vesicles, or liposomes, have multiple positive charges on the surface which allow them to form a complex with a polynucleotide or other anionic molecule such as negatively charged proteins. Remaining net cationic charges on the surface of the polynucleotide/cytofectin/neutral lipid complex are capable of strong interaction with the predominately negative charge of the cell membrane surface.

Apart from the basic features of amphiphilic properties and the polar head group, cytofectins have considerable structural diversity in the lipophilic and hydrophilic regions. Many different cytofectin species have been synthesized for use in transfection and are now commercially available. Such cytofectins include, for example, Lipofectin™, Lipofectin ACE™, LipofectAMINE™, Transfeactam™, and DOTAP™. The structural diversity of effective cytofectins reflects, in part, the observation that structure-function-recognition aspects of cytofectins differ with respect to distinct applications in cells. Experience with cytofectins structurally similar to the DOTMA compounds indicates that transfection activity depends in part on the cell type transfected (Felgner et al. *J. Biol. Chem.* 84:7413–7417, 1987; Wheeler et al. *Biochem. Biophys. Acta*, in press). Particularly, cationic lipids comprising spermine substitution of the ammonium groups proved more effective than DOTMA for transfection of some cell lines. This phenomenon suggests that effective transfection depends not only on passive fusion of the cationic lipid complex with the structural lipid bilayer of the plasma membrane, but on specific cellular characteristics and interaction between cell components and the individual cationic lipid species.

Structural variants among cytofectin species are therefore an indication of a more sophisticated understanding of the multiple and complex interactions of cytofectins with cells, and an effort on the part of investigators to take advantage of one or more of these interactions.

DOTMA, N-[1-(2,3-dioleyloxy)propyl]-N,N,N-trimethylammonium, disclosed in U.S. Pat. No. 5,049,386 to Epstein, was one of the first cationic lipids developed, and lipids of this group have become reference compounds in evaluating comparative cytofectin potency in the development of new structural variants. DOTMA lipids are characterized by a propanaminium group having a quaternary nitrogen, which provides the cationic site of the molecule, together with a pair of $C_{18}$ hydrocarbons that are ether-linked to the propyl backbone of the molecule. The quaternary nitrogen is trisubstituted with relatively shorter alkyl chains, such as methyl groups. A structurally similar cationic lipid, 1,2-bis(oleoyloxy)-3-3-(trimethylammonia)propane (DOTAP), comprises acyl, rather than ether-linked alkyl groups, and is believed to be more easily metabolized by target cells.

Some species of cationic lipids, for example, ammonium salts directly substituted by alkyl or acyl groups, were developed primarily for purposes of economy (U.S. Pat. No. 5,279,833 to Rose). Others were developed in an effort to provide less toxic effects; for example, a highly biocompatible cytofectin prepared from phosphatidylcholine and sphingomyelin: 1,2-dioleoyl-sn-glycero-3-ethylphosphocholine (Avanti Polar Lipids, Inc. Alabaster, Ala., Cat. Nos. 890700-706).

U.S. Pat. No. 5,264,618 to Felgner et al., the contents of which are incorporated herein by reference, discloses cytofectins that are structurally similar to the Rosenthal Inhibitor (RI) of phospholipase A (Rosenthal et al., *J. Biol. Chem.* 235:2202–2206, 1960) and diacyl- or alkyl/acyl-species thereof. The RI based series of compounds are known by acronyms having the pattern: DORIE ($C_{18}$); DPRIE ($C_{16}$); and DMRIE ($C_{14}$). These acronyms imply a common basic chemical structure; for example, DMRIE is 1-propanaminium, N-(2-hydroxyethyl)-N,N-dimethyl-2,3-bis(tetradecyloxy)-bromide, (±)-(CAS registry:146659); the others differ in their substituent alkyl groups. These cytofectins, having a polar hydroxyethyl substituent on the quaternary ammonium group, provide more effective transfection in many cases than DOTMA type compounds. A study of the effect of varying substituents at the hydroxyalkyl moiety and variation of alkyl chain lengths on the transfection efficacy of the RI cytofectins is presented in Felgner et al. (*J. Biol. Chem.* 269:2550–2561, 1994). Again, the studies showed that the optimum hydroxyl alkyl chain length is cell-type dependent.

The conversion of DMRIE to βAE-DMRIE (Wheeler et al., Biochem. Biophys. Acta, in press) has been found to have a significant effect on cytofectin activity. DMRIE, which has a quaternary nitrogen adjacent to a primary alcohol, thus imparting a pH independent positive charge, is one of the most active cytofectins now known. However, the substitution of a primary amine group for the alcohol on DMRIE to give βAE-DMRIE was found to form DNA complexes that are structurally distinct from those with DMRIE, and βAE-DMRIE is able to transfect many cell lines effectively in the absence of helper co-lipids. The observation that a single substitution in the cytofectin skeleton can provide marked changes in transfection properties suggests that other modifications can bring about similar improvements in gene delivery.

Continuing studies of the transfection event indicate that cationic lipids may facilitate not only entry of the functional molecule into the cytoplasm of a cell, but may also provide additional beneficial capabilities; for example, protecting the functional molecule from lysosomal degradation, facilitating entry into the nuclear compartment, or even preventing the degradation of the RNA transcription product by cytoplasmic enzymes. These functions of cationic molecules are believed to be related to specific structural features. Accordingly, there is a need for cytofectins that are particularly suited to transfection of foreign molecules into specific cell types. There is also a need to develop cytofectins that are able to perform specific intracellular functions.

SUMMARY OF THE INVENTION

One embodiment of the present invention is a compound of the formula

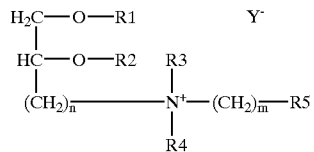

wherein
- $R_1$ and $R_2$ are independently H, linear or branched, unsubstituted or substituted $C_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0 to 4.
- $R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

$R_5$ has the structure

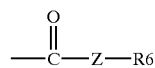

wherein
- Z is selected from the group consisting of O, S, $NR_1$, NH, Se, and $CR_7R_8$;
- $R_6$ is selected from the group consisting of absent, H, R1, R2, R3 and R4;
- n is 1 to 6;
- m is 1 to 10;
- Y is a pharmaceutically acceptable anion; and
- $R_7$ and $R_8$ independently or in combination are H or alkyl groups as defined for $R_1$ and $R_2$;
- wherein if Z is O, n is 1, and m is 3, then $R_6$ is selected from the group defined for $R_3$ and $R_4$ and wherein $R_1$ and $R_2$ are not both H.

In some aspects of this embodiment, m is 2–10.

In one aspect of this embodiment, $R_1$ and $R_2$ are $C_{10}$ to $C_{20}$ alkyl or alkenyl groups, Z is O and $R_6$ is an amino acid or peptide linked to Z as an ester.

In another aspect of this embodiment, Z is O, $R_1$ and $R_2$ are identical and are selected from the group consisting of $C_{14}H_{29}$ and $(CH_2)_8CH=CH(CH_2)_7CH_3$, and $R_3$ and $R_4$ are methyl.

In a further aspect of this embodiment, $R_1$ and $R_2$ are saturated or unsaturated $C_{10}$–$C_{18}$ alkyl groups.

In another aspect of this embodiment, $R_1$ and $R_2$ are identical and are selected from the group consisting of $C_{14}H_{29}$ and $C_{12}H_{25}$. In some of these compounds, $R_3$ and $R_4$ are selected from the group consisting of $C_1$–$C_5$ alkyl groups and $C_1$–$C_5$ heteroalkyl groups having one heteroatom therein. In other compounds, $R_3$ and $R_4$ are methyl groups.

Another embodiment of the present invention is a compound of the formula

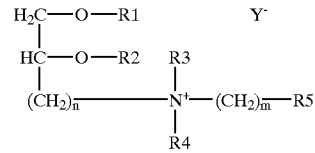

wherein
- $R_1$ and $R_2$ are independently H, linear or branched, unsubstituted or substituted $C_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;
- $R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N((CH$_2$)$_k$—CH$_3$)$_2$, wherein the alkyl groups of said substituents comprise from 0 to 2 heteroatoms and k is 0–4;

wherein R$_5$ has the structure

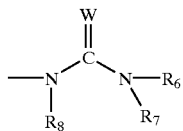

wherein

R$_6$, or R$_6$ together with R$_7$, is selected from the group defined for R$_1$, R$_2$, R$_3$ and R$_4$ and optionally further comprises a chemically linked amino acid, peptide, polypeptide, protein, nucleic acid, nucleotide, polynucleotide, mono, di- or polysaccharide, or other bioactive or pharmaceutical agent;

R$_8$ is absent, or is H or an alkyl group selected from the group consisting of R$_1$, R$_2$, R$_3$ and R$_4$ and wherein R$_8$ may be joined to R$_6$ or R$_7$ so as to form a ring;

W is O, NR$_{10}$, NH, S, or Se;

R$_{10}$ is an alkyl group as defined for R$_1$ and R$_2$;

n is 1 to 6;

m is 1 to 10; and

Y is a pharmaceutically acceptable anion;

wherein R$_1$ and R$_2$ are not both H.

In some aspects of this embodiment, m is 2–10.

In some aspects of this embodiment, R$_1$ and R$_2$ are saturated or unsaturated C$_{10}$–C$_{18}$ alkyl groups. In some of these compounds, R$_1$ and R$_2$ are identical and are selected from the group consisting of C$_{14}$H$_{29}$ and C$_{12}$H$_{25}$. In other compounds, R$_3$ and R$_4$ are selected from the group consisting of C$_1$–C$_5$ alkyl groups and C$_1$–C$_5$ heteroalkyl groups having one heteroatom therein. In additional compounds, R$_3$ and R$_4$ are methyl groups.

Another embodiment of the present invention is a compound of the formula

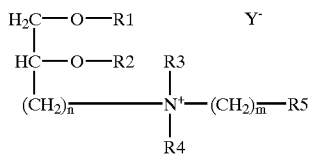

wherein

R$_1$ and R$_2$ are independently H, linear or branched, unsubstituted or substituted C$_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—(CH$_2$)$_k$—CH$_3$, S—(CH$_2$)$_k$—CH$_3$, X—(CH$_2$)$_k$—, wherein X is a halide, and —N((CH$_2$)$_k$—CH$_3$)$_2$, wherein the alkyl groups of said substituents comprise from 0 to 2 heteroatoms is 0–4, n is 1–6, and m is 1–10; and R$_3$ and R$_4$ are independently linear or branched, unsubstituted or substituted C$_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—(CH$_2$)$_k$—CH$_3$, —S—(CH$_2$)$_k$—CH$_3$, X—(CH$_2$)$_k$—, wherein X is a halide, and —N((CH$_2$)$_k$—CH$_3$)$_2$, wherein the alkyl groups of said substituents comprise from 0 to 2 heteroatoms and k is 0–4;

wherein R$_5$ is —O—R$_6$ such that R$_5$—O—R$_6$ comprises an ether linkage, wherein R$_6$ is selected from the group consisting of amino acids, peptides, polypeptides, proteins, nucleic acids, nucleotides, polynucleotides, monosaccharides, disaccharides, polysaccharides, bioactive agents, pharmaceutical agents, and linear or branched, unsubstituted or substituted C$_{1-23}$ heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—(CH$_2$)$_k$—CH$_3$, —S—(CH$_2$)$_k$—CH$_3$, X—(CH$_2$)$_k$—, wherein X is a halide, and —N((CH$_2$)$_k$—CH$_3$)$_2$, wherein the alkyl groups of said substituents comprise from 0 to 2 heteroatoms and k is 0–4;

n is 1 to 6;

m is 1 to 10; and

Y is a pharmaceutically acceptable anion; and wherein R$_1$ and R$_2$ are not both H.

In some aspects of this embodiment, m is 2–10.

In some aspects of this embodiment, R$_1$ and R$_2$ are both alkyl groups or are both alkenyl groups and R$_6$ comprises an amino acid or peptide selected from the group consisting of amino acids and peptides which are non-polar, amino acids and peptides which are polar and uncharged, and amino acids and peptides which are negatively charged at physiological pH. In some of these compounds, R$_1$ and R$_2$ are both alkyl groups or are both alkenyl groups and R$_6$ comprises a bioactive moiety.

In other compounds, R$_5$ is selected from the group consisting of monosaccharides, disaccharides, and polysaccharides.

In further compounds, R$_1$ and R$_2$ are saturated or unsaturated C$_{10}$–C$_{18}$ alkyl groups. In some of these compounds, R$_1$ and R$_2$ are identical and are selected from the group consisting of C$_{14}$H$_{29}$ and C$_{12}$H$_{25}$. In additional compounds, R$_3$ and R$_4$ are selected from the group consisting of C$_1$–C$_5$ alkyl groups and C$_1$–C$_5$ heteroalkyl groups having one heteroatom therein. In further compounds, R$_3$ and R$_4$ are methyl groups.

Another embodiment of the present invention is a compound having the structure

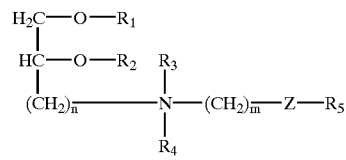

wherein

R$_1$ and R$_2$ are independently H, linear or branched, unsubstituted or substituted C$_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—(CH$_2$)$_k$—CH$_3$, —S—(CH$_2$)$_k$—CH$_3$, X—(CH$_2$)$_k$—, wherein X is a halide, and —N((CH$_2$)$_k$—CH$_3$)$_2$, wherein the alkyl groups of said substituents comprise from 0 to 2 heteroatoms and k is 0–4;

$R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

wherein $R_5$ is selected from the group defined for $R_3$ and $R_4$ and optionally further comprises a chemically linked amino acid, peptide, polypeptide, protein, nucleic acid, nucleotide, polynucleotide, monosaccharide, disaccharide or polysaccharide, or other bioactive or pharmaceutical agent; and Z is NH, or S;

n is 1 to 6;

m is 1 to 10; and

Y is a pharmaceutically acceptable anion;

wherein $R_1$ and $R_2$ are not both H, and wherein if Z is NH and n is 1 and m is 2 to 6, and $R_1$ and $R_2$ separately or together are $C_1$–$C_{23}$ alkyl or C(O)—$C_1$–$C_{23}$, and $R_3$ and $R_4$ separately or together are H or unbranched alkyl $C_1$–$C_6$, then $R_5$ is not —$(CH_2)_z NH_2$ where z is 2–6; or —$(CH_2)_3$—NH—$(CH_2)_4$—$NH_2$; or —NH—$(CH_2)_3$—NH—$(CH_2)_4$—NH$(CH_2)_3$—$NH_2$, C(O)-fluorescein, or

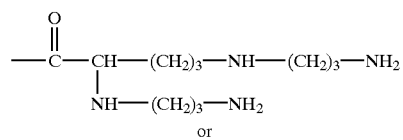

or

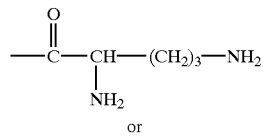

or

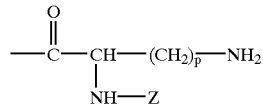

where p is 2–5, Z is H or other groups attached by amide or alkyl amino groups.

In some aspects of this embodiment, m is 2–10.

In one aspect of this embodiment, $R_1$ and $R_2$ are saturated or unsaturated $C_{10}$–$C_{18}$ alkyl groups. In some of these compounds, $R_1$ and $R_2$ are identical and are selected from the group consisting of $C_{14}H_{29}$ and $C_{12}H_{25}$. In other compounds, $R_3$ and $R_4$ are selected from the group consisting of $C_1$–$C_5$ alkyl groups and $C_1$–$C_5$ heteroalkyl groups having one heteroatom therein. In additional compounds, $R_3$ and $R_4$ are methyl groups. Another embodiment of the present invention is a compound having the structure:

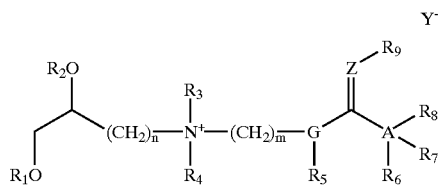

wherein $R_1$ and $R_2$ are independently H, linear, branched, unsubstituted or substituted $C_{1-23}$ alkyl, acyl, alkylene, or heteroalkyl groups having from 0 to 6 sites of unsaturation, or cyclic or aryl groups, said cyclic or aryl groups containing up to five heteroatoms, wherein the substituent groups are selected from the group consisting of —O—$(CH_2)_k$—$CH_3$, —S—$(CH_2)_k$—$CH_3$, X—$(CH_2)_k$—, wherein k is 0 to 4, wherein X is a halide, and —N$((CH_2)_k$—$CH_3)_2$, wherein the alkyl groups of said substituents comprise from 0 to 2 heteroatoms;

$R_3$ and $R_4$ are independently linear, branched, unsubstituted or substituted $C_{1-23}$ alkyl, acyl, alkene, or heteroalkyl groups having from 0 to 6 sites of unsaturation, or cyclic or aryl groups, said cyclic or aryl groups containing up to five heteroatoms, wherein the substituent groups are selected from the group consisting of —O—$(CH_2)_k$—$CH_3$, —S—$(CH_2)_k$—$CH_3$, X—$(CH_2)_k$—, wherein k is 0 to 4, wherein X is a halide, and —N$((CH_2)_k$—$CH_3)_2$, wherein the alkyl groups of said substituents comprise from 0 to 2 heteroatoms and k is 0 to 4;

$R_5$ is absent, H or an alkyl group as defined for $R_1$ and $R_2$; $R_5$ through $R_{10}$ independently or in combination are absent, or are H or alkyl groups as defined for $R_1$ and $R_2$ and, optionally, further comprise a chemically linked amino acid, peptide, polypeptide, protein, nucleic acid, nucleotide, polynucleotide, mono-, di- or polysaccharide, or other bioactive or pharmaceutical agent;

G is absent, O, N, S or Se;

Z is O, N, S, or Se;

A is O, N, S, Se, or C;

n is 1–6;

m is 1–10;

Y is a pharmaceutically acceptable anion;

wherein if G is N and Z is O, then A is not C;

wherein if G is O and Z is O then A is not C;

wherein if G is absent, Z is O, A is O, $R_6$ and $R_7$ are absent, n is 1, and m is 3, then $R_8$ is not absent or H;

wherein $R_1$ and $R_2$ are not both H;

and wherein if G is NH and n is 1 and m is 2 to 6, and $R_1$ and $R_2$ separately or together are $C_1$–$C_{23}$ alkyl or alkenyl or C(O)—$C_1$–$C_{23}$ alkyl or alkenyl, and $R_3$ and $R_4$ separately or together are H or unbranched alkyl $C_1$–$C_6$, and Z is O then A is not fluorescein, or

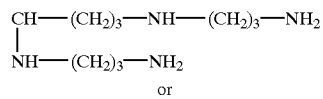

or

-continued $$\begin{array}{c} \text{CH}\!-\!\!(CH_2)_3\!-\!\!NH_2 \\ | \\ NH_2 \end{array}$$

or $$\begin{array}{c} \text{CH}\!-\!\!(CH_2)p\!-\!\!NH_2 \\ | \\ NH\!-\!\!Z \end{array}$$

where p is 2–5, Z is H or other groups attached by amide or alkyl amino groups.

In some aspects of this embodiment, m is 2–10.

One aspect of this embodiment is compounds having a primary amine within 8 atoms of the quaternary nitrogen.

In another aspect of this embodiment, if any of $R_5$–$R_{10}$ are amino acids or peptides they are selected from the group consisting of those amino acids and peptides which are non-polar, amino acids and peptides which are polar and uncharged, and amino acids and peptides which are negatively charged at physiological pH.

In yet another aspect of this embodiment, if any of $R_5$–$R_{10}$ are amino acids or peptides they comprise at least one amino acid not generally found in natural organisms.

In another aspect of this embodiment, $R_1$ and $R_2$ are saturated or unsaturated $C_{10}$–$C_{18}$ alkyl groups. In some of these compounds, $R_1$ and $R_2$ are identical and are selected from the group consisting of $C_{14}H_{29}$ and $C_{12}H_{25}$. In other compounds, $R_3$ and $R_4$ are selected from the group consisting of $C_1$–$C_5$ alkyl groups and $C_1$–$C_5$ heteroalkyl groups having one heteroatom therein. In additional compounds, $R_3$ and $R_4$ are methyl groups.

Another embodiment of the present invention is a cytofectin formulation comprising the compounds having the above formula in a physiologically or isotonically acceptable solution.

Another embodiment of the present invention is a cytofectin formulation comprising the cationic lipids having the above formula and a co-lipid selected from the group consisting of neutral lipids, phospholipids, and cholesterol in a suitable carrier solution.

Another embodiment of the present invention is a compound having the structure:

$$\begin{array}{c} R_1O \quad\quad R_3 \quad\quad\quad Y^- \\ \diagdown\!\!\diagup\!\!\!\diagdown\!\!\!\overset{\oplus}{N}\!\!-\!(CH_2)_{\overline{m}}\!-\!X_1 \\ R_2O \quad\quad\quad | \\ \quad\quad\quad (CH_2)_{\overline{n}}\!-\!X_2 \end{array}$$

wherein $R_1$ and $R_2$ are independently H, linear or branched, unsubstituted or substituted $C_{1\text{-}23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0 to 4;

$R_3$ is a linear or branched, unsubstituted or substituted $C_{1\text{-}23}$ alkyl, alkylene or heteroalkyl group having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0 to 4;

$X_1$ and $X_2$ are independently selected from the group consisting of $NR_4R_5$ and $OR_4$, wherein $R_4$ and $R_5$ are selected from the group consisting of $R_1$ as defined above, amino acids, peptides, polypeptides, proteins, nucleic acids, nucleotides, polynucleotides, monosaccharides, disaccharides, polysaccharide, other bioactive agents and other pharmaceutical agents;

n is 1 to 8;

m is 1 to 8;

wherein $R_1$ and $R_2$ are not both H.

In some aspects of this embodiment, $R_1$ and $R_2$ are saturated or unsaturated $C_{10}$–$C_{18}$ alkyl groups. In some of these compounds, $R_1$ and $R_2$ are identical and are selected from the group consisting of $C_{14}H_{29}$ and $C_{12}H_{25}$. In other compounds, $R_3$ is selected from the group consisting of $C_1$–$C_5$ alkyl groups and $C_1$–$C_5$ heteroalkyl groups having one heteroatom therein and n and m are 1–5. In further compounds, $R_3$ is a methyl group. In additional compounds X1 and X2 are $NR_4R_5$ and $R_4$ and $R_5$ are H. In other compounds, n and m are 2–5.

Another embodiment of the present invention is a compound of the formula:

$$\begin{array}{c} H_2C\!-\!O\!-\!R1 \quad\quad\quad\quad Y^- \\ | \\ HC\!-\!O\!-\!R2 \quad R3 \\ | \quad\quad\quad\quad\quad | \\ (CH_2)_{\overline{n}}\!\!-\!\!\!-\!\!\!-\!\!\!-\!\!\!\overset{+}{N}\!-\!(CH_2)_{\overline{m}}\!-\!R5 \\ \quad\quad\quad\quad | \\ \quad\quad\quad\quad R4 \end{array}$$

wherein $R_1$ and $R_2$ are saturated or unsaturated $C_{10}$–$C_{18}$ alkyl groups;

$R_3$ and $R_4$ are independently linear or branched, unsubstituted or substituted $C_{1\text{-}23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

$R_5$ has the structure $$\begin{array}{c} O \\ \| \\ -C\!-\!N\!\!\diagup\!\!\!\overset{R7}{\diagdown\!R8} \end{array}$$

$R_7$ and $R_8$ are independently selected from the group defined for $R_1$, $R_2$, $R_3$ and $R_4$ and optionally further comprise a chemically linked amino acid, peptide, polypeptide, protein, nucleic acid, nucleotide, polynucleotide, mono-, di- or polysaccharide, or other bioactive or pharmaceutical agent;

n is 1 to 6;

m is 1 to 10; and

Y is a pharmaceutically acceptable anion.

In some aspects of this embodiment, m is 2–10.

In one aspect of this embodiment, $R_1$ and $R_2$ are identical and are selected from the group consisting of $C_{14}H_{29}$ and $C_{12}H_{25}$. In some of these compounds, $R_3$ and $R_4$ are selected from the group consisting of $C_1$–$C_5$ alkyl groups and $C_1$–$C_5$ heteroalkyl groups having one heteroatom therein. In other compounds, $R_3$ and $R_4$ are methyl groups.

Another embodiment of the present invention is a compound of the formula:

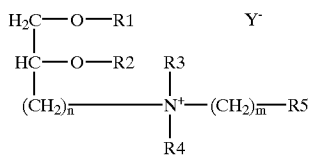

wherein $R_1$ and $R_2$ are saturated or unsaturated $C_{10}$–$C_{18}$ alkyl groups;

$R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

$R_5$ has the structure

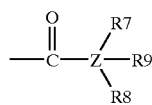

Z is C;

$R_7$, $R_8$ and $R_9$ are independently selected from the group defined for $R_1$, $R_2$, $R_3$ and $R_4$ and optionally further comprise a chemically linked amino acid, peptide, polypeptide, protein, nucleic acid, nucleotide, polynucleotide, mono-di- or polysaccharide, or other bioactive or pharmaceutical agent;

n is 1 to 6;

m is 1 to 10; and

Y is a pharmaceutically acceptable anion.

In some aspects of this embodiment, m is 2–10.

In one aspect of this embodiment, $R_1$ and $R_2$ are identical and are selected from the group consisting of $C_{14}H_{29}$ and $C_{12}H_{25}$. In some of these compounds, $R_3$ and $R_4$ are selected from the group consisting of $C_1$–$C_5$ alkyl groups and $C_1$–$C_5$ heteroalkyl groups having one heteroatom therein. In other compounds, $R_3$ and $R_4$ are methyl groups.

Another embodiment of the present invention is a compound of the formula

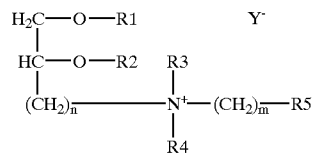

wherein $R_1$ and $R_2$ are saturated or unsaturated $C_{10}$–$C_{18}$ alkyl groups;

$R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

wherein $R_5$ has the structure

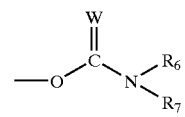

wherein $R_6$ or $R_6$ together with $R_7$ are selected from the group defined for $R_1$, $R_2$, $R_3$ and $R_4$ and optionally further comprises a chemically linked amino acid, peptide, polypeptide, protein, nucleic acid, nucleotide, polynucleotide, mono, di- or polysaccharide, or other bioactive or pharmaceutical agent;

W is O, $NR_8$, NH, S, or Se;

$R_8$ is an alkyl group as defined for $R_1$ and $R_2$;

n is 1 to 6;

m is 1 to 10; and

Y is a pharmaceutically acceptable anion.

In some aspects of this embodiment, m is 2–10.

In one aspect of this embodiment, $R_1$ and $R_2$ are identical and are selected from the group consisting of $C_{14}H_{29}$ and $C_{12}H_{25}$. In some of these compounds, $R_3$ and $R_4$ are selected from the group consisting of $C_1$–$C_5$ alkyl groups and $C_1$–$C_5$ heteroalkyl groups having one heteroatom therein. In additional compounds, $R_3$ and $R_4$ are methyl groups Another embodiment of the present invention is a compound of the formula

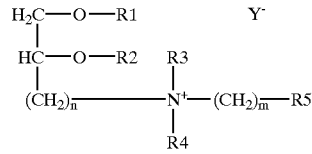

wherein $R_1$ and $R_2$ are saturated or unsaturated $C_{10}$–$C_{18}$ alkyl groups;

$R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

wherein $R_5$ has the structure

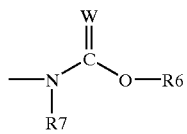

wherein
$R_6$, or $R_6$ together with $R_7$, is selected from the group defined for $R_1$, $R_2$, $R_3$ and $R_4$ and optionally further comprises a chemically linked amino acid, peptide, polypeptide, protein, nucleic acid, nucleotide, polynucleotide, mono, di- or polysaccharide, or other bioactive or pharmaceutical agent;

W is O, $NR_8$, NH, S, or Se;

$R_8$ is an alkyl group as defined for $R_1$ and $R_2$;

n is 1 to 6;

m is 1 to 10; and

Y is a pharmaceutically acceptable anion.

In some aspects of this embodiment, m is 2–10.

In one aspect of this embodiment, $R_1$ and $R_2$ are identical and are selected from the group consisting of $C_{14}H_{29}$ and $C_{12}H_{25}$. In some of these compounds, $R_3$ and $R_4$ are selected from the group consisting of $C_1$–$C_5$ alkyl groups and $C_1$–$C_5$ heteroalkyl groups having one heteroatom therein. In additional compounds, $R_3$ and $R_4$ are methyl groups.

Another embodiment of the present invention is a compound of the formula

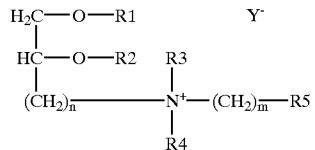

wherein
$R_1$ and $R_2$ are saturated or unsaturated $C_{10}$–$C_{18}$ alkyl groups;

$R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

wherein $R_5$ is NH—$R_6$–$R_7$, wherein $R_6$, or $R_6$ together with $R_7$, is selected from the group defined for $R_1$, $R_2$, $R_3$ and $R_4$ and optionally further comprises a chemically linked amino acid, peptide, polypeptide, protein, nucleic acid, nucleotide, polynucleotide, mono, di- or polysaccharide, or other bioactive or pharmaceutical agent;

n is 1–6;

m is 1–10; and

Y is a pharmaceutically acceptable anion; and wherein if n is 1, and m is 2 to 6, and $R_1$ and $R_2$ separately or together are $C_1$–$C_{23}$ alkyl or C(O)—$C_1$–$C_{23}$, and $R_3$ and $R_4$ separately or together are H or unbranched alkyl $C_1$–$C_6$, and $R_5$ is NH—$R_6$–$R_7$ then $R_6$–$R_7$ is not —$(CH_2)_z$NH$_2$ where z is 2–6; or —$(CH_2)_3$—NH—$(CH_2)_4$—NH$_2$; or —NH—$(CH_2)_3$—NH—$(CH_2)_4$—NH$(CH_2)_3$—NH$_2$, C(O)-fluorescein, or

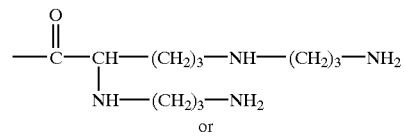

or

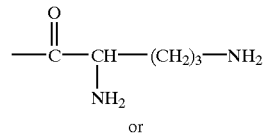

or

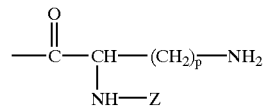

where
p is 2–5, Z is H or other groups attached by amide or alkyl amino groups.

In some aspects of this embodiment, m is 2–10.

In one aspect of this embodiment, $R_1$ and $R_2$ are identical and are selected from the group consisting of $C_{14}H_{29}$ and $C_{12}H_{25}$. In some of these compounds, $R_3$ and $R_4$ are selected from the group consisting of $C_1$–$C_5$ alkyl groups and $C_1$–$C_5$ heteroalkyl groups having one heteroatom therein. In additional compounds, $R_3$ and $R_4$ are methyl groups.

Another embodiment of the present invention is a method of delivering an anionic molecule into a cell comprising the steps of (a) contacting the anionic molecule with a formulation comprising an effective amount of any of the cationic lipids of the following structure to form a complex with the lipid:

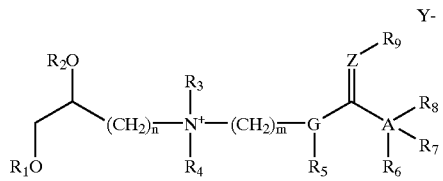

wherein
$R_1$ and $R_2$ are independently H, linear, branched, unsubstituted or substituted $C_{1-23}$ alkyl, acyl, alkylene, or heteroalkyl groups having from 0 to 6 sites of unsaturation, or cyclic or aryl groups, said cyclic or aryl groups containing up to five heteroatoms, wherein the substituent groups are selected from the group consisting of —O—$(CH_2)_k$—$CH_3$, —S—$(CH_2)_k$—$CH_3$, X—$(CH_2)_k$—, wherein k is 0 to 4, wherein X is a halide, and —N$((CH_2)_k$—$CH_3)_2$, wherein the alkyl groups of said substituents comprise from 0 to 2 heteroatoms;

$R_3$ and $R_4$ are independently linear, branched, unsubstituted or substituted $C_{1-23}$ alkyl, acyl, alkene, or heteroalkyl groups having from 0 to 6 sites of unsaturation, or cyclic or aryl groups, said cyclic or aryl groups containing up to five heteroatoms, wherein the substituent groups are selected from the group consisting of —O—$(CH_2)_k$—$CH_3$, —S—$(CH_2)_k$—$CH_3$, X—$(CH_2)_k$—, wherein k is 0 to 4, wherein X is a halide, and —N$((CH_2)_k$—$CH_3)_2$, wherein the alkyl groups of said substituents comprise from 0 to 2 heteroatoms and k is 0 to 4;

$R_5$ is absent, H or an alkyl group as defined for $R_1$ and $R_2$; $R_5$ through $R_{10}$ independently or in combination are absent, or are H or alkyl groups as defined for $R_1$ and $R_2$ and, optionally, further comprise a chemically linked amino acid, peptide, polypeptide, protein, nucleic acid, nucleotide, polynucleotide, mono-, di- or polysaccharide, or other bioactive or pharmaceutical agent;

G is absent, O, N, S or Se;

Z is O, N, S, or Se;

A is O, N, S, Se, or C;

n is 1–6;

m is 1–10;

Y is a pharmaceutically acceptable anion;

wherein if G is N and Z is O, then A is not C;

wherein if G is O and Z is O then A is not C;

wherein if G is absent, Z is O, A is O, $R_6$ and $R_7$ are absent, n is 1, and m is 3, then $R_8$ is not absent or H;

wherein $R_1$ and $R_2$ are not both H;

and wherein if G is NH and n is 1 and m is 2 to 6, and $R_1$ and $R_2$ separately or together are $C_1$–$C_{23}$ alkyl or alkenyl or C(O)—$C_1$–$C_{23}$ alkyl or alkenyl, and $R_3$ and $R_4$ separately or together are H or unbranched alkyl $C_1$–$C_6$, and Z is O then A is not fluorescein, or

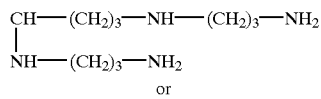

or

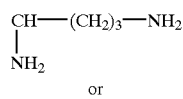

or

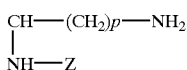

where p is 2–5, Z is H or other groups attached by amide or alkyl amino groups.

The method also comprises (b) contacting a cell with the lipid complex formed in step (a);

whereby a biologically effective amount of the anionic molecules are inserted into the cell. In one aspect of this embodiment, the cells are in vitro. In another aspect of this embodiment, the cells are in vivo. For example, the cells may be in an assay selected from the group consisting of murine lung transfection, murine intraperitoneal tumor, murine intramuscular and porcine or rabbit intraarterial.

Another embodiment of the present invention is a method of delivering an anionic molecule into a cell comprising the steps of (a) contacting the anionic molecule with a formulation comprising an effective amount of any of the cationic lipids of the following formula to form a complex with the lipid:

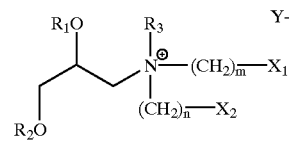

wherein $R_1$ and $R_2$ are independently H, linear or branched, unsubstituted or substituted $C_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0 to 4;

$R_3$ is a linear or branched, unsubstituted or substituted $C_{1-23}$ alkyl, alkylene or heteroalkyl group having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0 to 4;

$X_1$ and $X_2$ are independently selected from the group consisting of $NR_1R_5$ and $OR_4$, wherein $R_4$ and $R_5$ are selected from the group consisting of $R_1$ as defined above, amino acids, peptides, polypeptides, proteins, nucleic acids, nucleotides, polynucleotides, monosaccharides, disaccharides, polysaccharide, other bioactive agents and other pharmaceutical agents;

n is 1 to 8;

m is 1 to 8;

wherein $R_1$ and $R_2$ are not both H.

The method also comprises (b) contacting a cell with the lipid complex formed in step (a);

whereby a biologically effective amount of the anionic molecules are inserted into the cell.

BRIEF DESCRIPTION OF REACTION SCHEMES

Figure 1A:
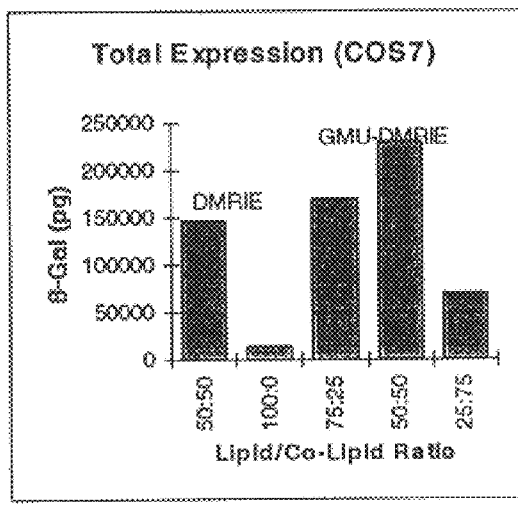
FIG. 1A is a graph of the level of total β-gal expression obtained in COS7 cells with different ratios of GMU-DMRIE:DOPE.
Figure 1B:
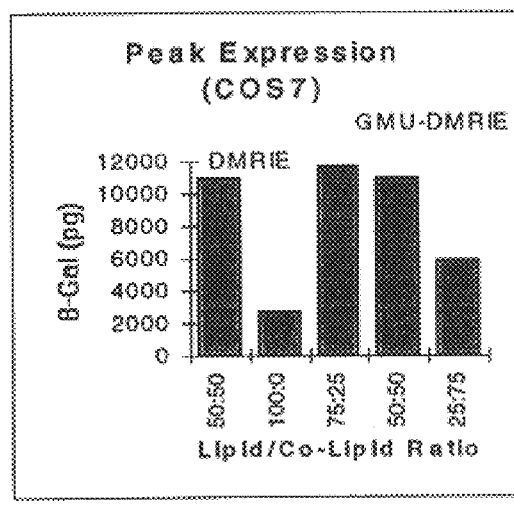
FIG. 1B is a graph of the peak β-gal expression obtained in COS7 cells with different ratios of GMU-DMRIE:DOPE.
Figure 1C:
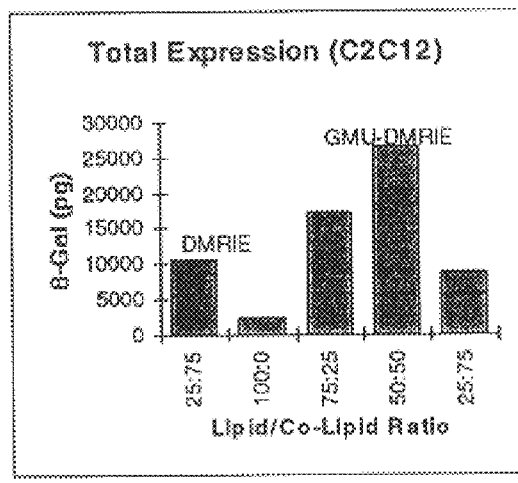
FIG. 1C is a graph of the total β-gal expression obtained in C2C12 cells with different ratios of GMU-DMRIE:DOPE.
Figure 1D:
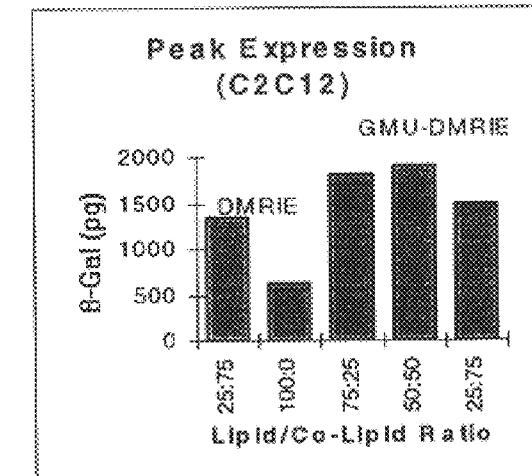
FIG. 1D is a graph of the peak β-gal expression obtained in C2C12 cells with different ratios of GMU-DMRIE:DOPE.

Following the text of the specification are several representative reaction schemes. These numbered reaction schemes illustrate the following:

Scheme I illustrates the synthetic pathway for the basic skeleton of the cytofectins of the present invention.

Scheme II illustrates routes for the preparation of intermediates from commercially available starting materials in the synthesis of the cytofectins of the invention.

Scheme III illustrates the synthetic pathway for carboxy cytofectins from an intermediate compound.

Scheme IV illustrates the synthetic pathway for carbamyl cytofectins from an intermediate compound.

Scheme V illustrates the synthetic pathway for cytofectins with urea-like functional groups from an intermediate compound.

Scheme VI illustrates the synthetic pathway for disubstituted RI cytofectins having two heterosubstituted groups on the quaternary nitrogen.

DETAILED DESCRIPTION OF THE PREFERRED EMBODIMENT

It has been discovered that amphipathic lipids of the quaternary ammonium class of cytofectins, for which the groups, for example, a ketone, ester, ureyl or carbamyl moiety. The functional group can be used either (1) to attach a cell targeting moiety or (2) to attach a therapeutic molecule to the cytofectin. Additionally or alternatively, the functional group can be used as a linker to attach groups that can increase the polar charge density of the cytofectin, thus enhancing transfection. For example, we have discovered that the presence of a primary amine group within 8 carbons of the quaternary nitrogen has been found to enhance transfection efficiency. Examples of effective cytofectins having a primary amine within 8 carbons of the quaternary nitrogen are disclosed in Examples 7 and 9, and the results shown in FIGS. 2, 3, 4, and 5.

Despite the original presumption that only positively charged amino acids or peptides would be capable of increasing cytofectin efficiency (see U.S. Pat. No. 5,264,618), transfection efficiency may also be enhanced by linking a peptide or amino acid which is non-polar, polar and uncharged, or negatively charged at physiological pH to the Rosenthal Inhibitor backbone. For example, the uncharged amino acid glycine confers greater transfection activity when linked to DLRIE than does the charged amino acid lysine.

Nomenclature

The cytofectins of the invention are cationic lipid species which have the core structure of the RI, DL-2,3-diacyloxypropyl(dimethyl)-β-hydroxyethylammonium

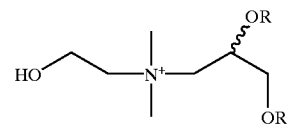

Examples of acronyms for the RI class of cytofectins are:

| | | |
|---|---|---|
| DORI: | DiOleylRosenthalInhibitor | R = CO(CH$_2$)$_7$[z]CH=(CH$_2$)$_7$CH$_3$ |
| DORIE: | DiOleylRosenthalInhibitorEther | R = (CH$_2$)$_8$[z]CH=CH(CH$_2$)$_7$CH$_3$ |
| DDRIE: | DiDecylRosenthalInhibitorEther | R = (CH)$_9$CH$_3$ |
| DLRIE: | DiLaurylRosenthalInhibitorEther | R = (CH$_2$)$_{11}$CH$_3$ |
| DMRIE: | DiMyristylRosenthalInhibitorEther | R = (CH$_2$)$_{13}$CH$_3$ |
| DPRIE: | DiPalmitylRosenthalInhibitorEther | R = (CH$_2$)$_{15}$CH$_3$ |
| DSRIE: | DiStearylRosenthalInhibitorEther | R = (CH$_2$)$_{17}$CH$_3$ |
| βAE-DMRIE: | β-AminoEthylDiMyristylRosenthalInhibitorEther | |
| DMRIE-Ox: | DiMyristylRosenthalInhibitorEtherCarboxylate | |

Rosenthal Inhibitor (RI) series is the paradigm, can be derivatized to form highly effective transfection agents having the ability to interact more specifically with the cell membrane and to achieve higher levels of transfection. They provide structures that can be adapted to target key receptors and enzymes of cellular surfaces and are thus suitable for use in the discovery and exploitation of important factors in molecular recognition. Some of these cationic lipids can also be attached to substances that are delivered intracellularly for achieving a particular biological purpose.

The cationic lipids of the present invention have chemical structures comprising the DOTMA or RI features as described previously, but have attached thereto, through a linking spacer, a structure advantageously having functional Similar acronyms denote neutral lipids contained in liposomal formulations, for example:

DOPE: DiOleoylPhosphatidylEthanolamine

Cytofectins of the Invention: Structure

In one embodiment, the lipids of the invention have the general structure:

(Formula 1)

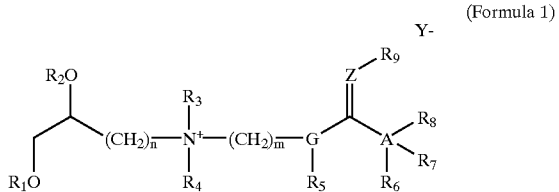

wherein

- $R_1$ and $R_2$ are independently H, linear, branched, unsubstituted or substituted $C_{1-23}$ alkyl, acyl, alkylene, or heteroalkyl groups having from 0 to 6 sites of unsaturation, or cyclic or aryl groups, said cyclic or aryl groups containing up to five heteroatoms, wherein the substituent groups are selected from the group consisting of $-O-(CH_2)_k-CH_3$, $-S-(CH_2)_k-CH_3$, $X-(CH_2)_k-$, wherein k is 0 to 4, wherein X is a halide, and $-N((CH_2)_k-CH_3)_2$, wherein the alkyl groups of said substituents comprise from 0 to 2 heteroatoms;
- $R_3$ and $R_4$ are independently linear, branched, unsubstituted or substituted $C_{1-23}$ alkyl, acyl, alkene, or heteroalkyl groups having from 0 to 6 sites of unsaturation, or cyclic or aryl groups, said cyclic or aryl groups containing up to five heteroatoms, wherein the substituent groups are selected from the group consisting of $-O-(CH_2)_k-CH_3$, $-S-(CH_2)_k-CH_3$, $X-(CH_2)_k-$, wherein k is 0 to 4, wherein X is a halide, and $-N((CH_2)_k-CH_3)_2$, wherein the alkyl groups of said substituents comprise from 0 to 2 heteroatoms and k is 0 to 4;
- $R_5$ is absent, H or an alkyl group as defined for $R_1$ and $R_2$; $R_5$ through $R_9$ independently or in combination are absent, or are H or alkyl groups as defined for $R_1$ and $R_2$ and, optionally, further comprise a chemically linked amino acid, peptide, polypeptide, protein, nucleic acid, nucleotide, polynucleotide, mono-, di- or polysaccharide, or other bioactive or pharmaceutical agent;
- G is absent, O, N, S or Se;
- Z is O, N, S, or Se;
- A is O, N, S, Se, or C;
- n is 1–6;
- m is 1–10;
- Y is a pharmaceutically acceptable anion;
- wherein if G is N and Z is O, then A is not C;
- wherein if G is O and Z is O then A is not C;
- wherein if G is C and Z is C then A is not C;
- wherein if G is absent, Z is O, A is O, $R_6$ and $R_7$ are absent, n is 1, and m is 3, then $R_8$ is not absent or H;
- wherein $R_1$ and $R_2$ are not both H;
- and wherein if G is NH and n is 1 and m is 2 to 6, and $R_1$ and $R_2$ separately or together are $C_1$–$C_{23}$ alkyl or alkenyl or $C(O)-C_1-C_{23}$ alkyl or alkenyl, and $R_3$ and $R_4$ separately or together are H or unbranched alkyl $C_1$–$C_6$, and Z is O then A is not fluorescein, or

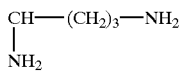

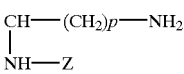

or

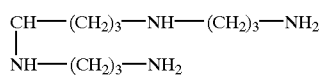

where p is 2–5, Z is H or other groups attached by amide or alkyl amino groups.

In one embodiment, the above compounds have a primary amine within 8 atoms of the quaternary nitrogen. In another embodiment of the above compounds m is 2–10.

In another embodiment, if any of $R_5$–$R_{10}$ are amino acids or peptides they are selected from the group consisting of those amino acids and peptides which are non-polar, amino acids and peptides which are polar and uncharged, and amino acids and peptides which are negatively charged at physiological pH.

In another embodiment, if any of $R_5$–$R_{10}$ are amino acids or peptides they comprise at least one amino acid not generally found in natural organisms.

In a further embodiment, $R_1$ and $R_2$ are saturated or unsaturated $C_{10}$–$C_{18}$ alkyl groups.

In some embodiments, $R_1$ and $R_2$ are identical and are selected from the group consisting of $C_{14}H_{29}$ and $C_{12}H_{25}$.

In further embodiments, $R_3$ and $R_4$ are selected from the group consisting of $C_1$–$C_5$ alkyl groups and $C_1$–$C_5$ heteroalkyl groups having one heteroatom therein.

In additional embodiments, $R_3$ and $R_4$ are methyl groups.

In a preferred embodiment of this structure, n=1–2. In another preferred embodiment, m=2–4. In a further preferred embodiment, k=0–4. Preferentially, $R_3$–$R_{10}$, if alkyl, are $C_{10}$–$C_{15}$.

In a preferred embodiment, the cytofectins of the present invention have the following formula:

(Formula 2)

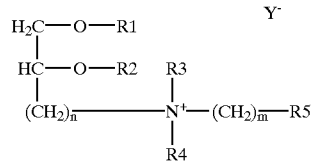

wherein $R_1$, $R_2$, $R_3$ and $R_4$ are independently linear or branched, unsubstituted or substituted $C_{1-23}$ alkyl, acyl, alkylene or heteroalkyl groups having from 0 to 6 sites of unsaturation, cyclic and aryl groups, and containing from 0 to 5 heteroatoms wherein said heteroatoms are not the first atoms in said groups, the substituent groups selected from $-O-(CH_2)_k-CH_3$, $-S-(CH_2)_k-CH_3$, $X-(CH_2)_k-$, wherein X is a halide, and $-N((CH_2)_k-CH_3)_2$, wherein the alkyl groups contain from 0 to 2 heteroatoms; n is 1 to 6; m is 2 to 10; and $R_5$ is a chemical structure having functional groups that define a species of formula 2. $R_5$ is preferably linked to the ammonium nitrogen through an alkyl linker, which can also contain heteroatoms.

The cationic lipids of the invention are associated with a physiologically acceptable non-toxic anion, Y. Anions commonly used in pharmaceutical preparations are disclosed in Berge et al. (*J. Pharm. Sci.* 66:1–19, 1977), which is hereby incorporated by reference.

In preferred embodiments, n is 1 and m is 2–4, and the preferred cytofectin species of the invention thus have the RI skeleton shown in the key intermediate, formula I-3, infra. Other cytofectin species of the present invention are homologs of the RI based group, and these cytofectins have the same general formula I; however, n is 3–6 and m is 1–10. In some embodiments, m is 2–10.

The cytofectins of the present invention can be viewed as an assembly of functional parts in a modular arrangement, comprising:

A. A hydrophobic structure, which can be aliphatic chains, that can include cyclic structures within, but not between, the aliphatic chains.

B. A most characteristic portion of the molecule, comprising a quaternary N atom substituted with dialkoxy, diacyloxy, and alkyl groups, that can also be part of a ring that includes the groups attached above and below in Formula 1.

C. A spacer, $(CH_2)_n$, that is usually an aliphatic chain, but can also include one or more heteroatoms.

D. A linker group, often a backbone of three atoms having a central carbon atom, usually doubled bonded to oxygen. The linker group is carboxyl, carbamyl, ureyl, or guanidyl, and, as will be considered below, may have a common key synthetic intermediate. In the molecules of the invention, when this group is not symmetrical, its left to right orientation can be reversed.

E. A "cargo" portion of the molecule, which can comprise amino acids, peptides, proteins, carbohydrates, nucleic acids, drugs, ligands, or any other molecular species that can interact with a cell constituent to induce a desired response. These molecules can be attached to the linker group of the molecule by bifunctional spacers.

Compounds of the class described above were designed to allow efficient derivatization of the basic dioxypropan-iminium skeleton with a wide variety of chemical moieties, and in particular those entities which are considered physiologically active. Members of this class of cytofectins have been constructed as paradigms for the general introduction of a wide variety of chemical functionalities using the synthetic methods disclosed herein. The unique functional groups described herein as "linkers" will also impart enhanced properties of efficacy and/or specificity to the cytofectins of the invention.

The specific bioactive peptides and saccharides introduced into the ureas and thioureas, respectively, will allow selective targeting or enhanced internalization via receptor-mediated processes. The introduction of a urea group will increase the interaction between the cytofectin and the phosphate backbone of DNA, thus enhancing transfection. The ability to generalize the disclosed procedures will allow easy functionalization of the basic cytofectin skeleton with a wide variety of bioactive molecules known to one of ordinary skill in the art.

Species of the cytofectins of the present invention are classified on the basis of a characteristic $R_5$ substitution in the general formula 1, as follows:

1. Carboxy Cytofectins

One species of cationic lipids of the invention is characterized by the presence of a carboxy group in a substituent linker group on the ammonium group of formula 1. The members of this class have the following structure:

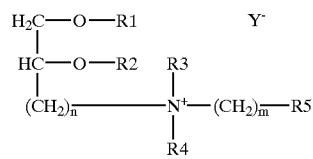

wherein $R_1$ and $R_2$ are independently H, linear or branched, unsubstituted or substituted $C_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0 to 4.

$R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

$R_5$ has the structure

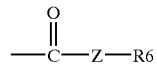

wherein

Z is selected from the group consisting of O, S, $NR_1$, NH, Se, and $CR_7R_8$;

$R_6$ is selected from the group consisting of absent, H, $R_1$, $R_2$, $R_3$ and $R_4$;

n is 1 to 6;

m is 1 to 10;

Y is a pharmaceutically acceptable anion; and $R_7$ and $R_8$ independently or in combination are H or alkyl groups as defined for $R_1$ and $R_2$;

wherein if Z is O, n is 1, and m is 3, then $R_6$ is selected from the group defined for $R_3$ and $R_4$ and wherein $R_1$ and $R_2$ are not both H.

In some embodiments of the above compounds, m is 2–10.

When Z is N, $R_5$ has the structure

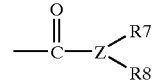

and when Z is C, $R_5$ has the structure

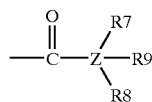

wherein
$R_7$, $R_8$ and $R_9$ are independently H or are selected from the group defined for $R_1$, $R_2$, $R_3$ and $R_4$.

In all members of this species $R_6$, $R_7$, $R_8$ and $R_9$ optionally further comprise a chemically linked amino acid, peptide, polypeptide, protein, nucleic acid, nucleotide, polynucleotide, mono-, di- or polysaccharide, or other bioactive or pharmaceutical agent.

2. Carbamyl Cytofectins

Another species of cationic lipids of the invention is characterized by the presence of a carbamyl group in one of the substituents on the ammonium group of formula 1 and the members of this class have the general structure:

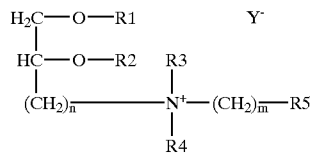

wherein
$R_1$ and $R_2$ are saturated or unsaturated $C_{10}$–$C_{18}$ alkyl groups;

$R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —$N((CH_2)_k$—$CH_3)_2$, wherein the alkyl groups of said substituents comprise from 0 to 2 heteroatoms and k is 0–4;

wherein $R_5$ has the structure

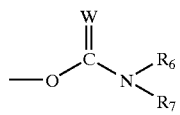

wherein
$R_6$ or $R_6$ together with $R_7$ are selected from the group defined for $R_1$, $R_2$, $R_3$ and $R_4$ and optionally further comprises a chemically linked amino acid, peptide, polypeptide, protein, nucleic acid, nucleotide, polynucleotide, mono, di- or polysaccharide, or other bioactive or pharmaceutical agent;

W is O, $NR_8$, NH, S, or Se;

$R_8$ is an alkyl group as defined for $R_1$ and $R_2$;

n is 1 to 6;

m is 1 to 10; and

Y is a pharmaceutically acceptable anion.

In some embodiments, m is 2 to 10.

The carbonyl cationic lipids of the invention also include those having the isomeric carbamyl structure wherein $R_5$ has the structure

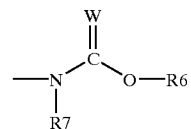

wherein
W is as defined above, $R_6$, is as defined for the carboxy species and $R_7$ is absent, or is H or an alkyl group as defined for the carboxy species. Preferred embodiments of the carbamate cytofectins comprise methyl carbamate groups attached to the lipid through alkyl linkers $(CH_2)_m$ wherein m is 2 to 4.

In other preferred embodiments $R_1$ and $R_2$ are saturated or unsaturated $C_{10}$–$C_{18}$ alkyl groups. In still further preferred embodiments, $R_1$ and $R_2$ are identical and are selected from the group consisting of $C_{14}H_{29}$ and $C_{12}H_{25}$. In other preferred embodiments, $R_3$ and $R_4$ are selected from the group consisting of $C_1$–$C_5$ alkyl groups and $C_1$ to $C_5$ heteroalkyl groups having one heteroatom therein. In other preferred embodiments $R_3$ and $R_4$ are methyl.

The carbamate structure allows facile amine-alcohol ligand coupling at the terminal group.

3. Cytofectins Having Urea-like Linking Groups

Another species of cationic lipids of the invention of is characterized by the presence of a urea-like group in a substituent on the ammonium group of formula 1 and the members of this class have the general structure:

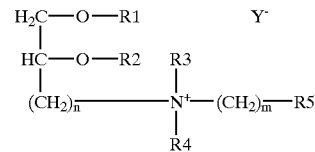

wherein
$R_1$ and $R_2$ are independently H, linear or branched, unsubstituted or substituted $C_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —$N((CH_2)_k$—$CH_3)_2$, wherein the alkyl groups of said substituents comprise from 0 to 2 heteroatoms and k is 0–4;

$R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —$N((CH_2)_k$—$CH_3)_2$, wherein the alkyl groups of said substituents comprise from 0 to 2 heteroatoms and k is 0–4;

wherein $R_5$ has the structure $$\begin{array}{c} W \\ \| \\ -N-C-N-R_6 \\ | \quad\quad | \\ R_8 \quad R_7 \end{array}$$

wherein
- $R_6$, or $R_6$ together with $R_7$, is selected from the group defined for $R_1$, $R_2$, $R_3$ and $R_4$ and optionally further comprises a chemically linked amino acid, peptide, polypeptide, protein, nucleic acid, nucleotide, polynucleotide, mono-, di- or polysaccharide, or other bioactive or pharmaceutical agent;
- $R_8$ is absent, or is H or an alkyl group selected from the group consisting of $R_1$, $R_2$, $R_3$ and $R_4$ and wherein $R_8$ may be joined to $R_6$ or $R_7$ so as to form a ring;
- W is O, $NR_{10}$, NH, S, or Se;
- $R_{10}$ is an alkyl group as defined for $R_1$ and $R_2$;
- n is 1 to 6;
- m is 1 to 10; and
- Y is a pharmaceutically acceptable anion;
wherein $R_1$ and $R_2$ are not both H.

(a) Ureyl cytofectins

One species of the cationic lipids of the invention of this class thus has the general structure of formula 1 and is characterized by the presence of a ureyl group in the substituent on the ammonium nitrogen of formula 1. In this species $R_5$ has the structure as defined above wherein W is oxygen.

(b) Guanidyl cytofectins

Another species of cationic lipids of the invention according to this class are characterized by the presence of a guanidyl group in a substituent of the ammonium group nitrogen of formula 1 and have the general structure of formula 1 wherein $R_5$ has the structure as defined above wherein W is N or NH.

(c) Thiourea and selenourea cytofectins

The cationic lipids of the invention also include compounds having the general structure of formula 1 wherein $R_5$ has the structure as defined above wherein W is S or Se.

(d) Other urea-related cytofectins

The cationic lipids of the invention also include compounds having the general structure of formula 1 wherein $R_5$ is as defined above wherein W is C, CH, $CHR_1$, or $CR_1R_2$, wherein $R_1$ and $R_2$ are as defined for formula 1; $R_6$, $R_7$ and $R_8$ are selected from the group defined for $R_1$, $R_2$, $R_3$ and $R_4$ The urea/thiourea synthesis allows facile amine-amine ligand coupling, and provides a means to prepare saccharide and amino acid derivatives. Preferred saccharide derivatives that can be prepared via the thiourea linkage include glucose, galactose, lactose, and arabinose species.

The structures of representative urea-like cytofectins are provided below. Each of the urea-like cytofectins have the general structure.

$$\begin{array}{c} RO \quad\quad\quad CH_3 \\ \quad\quad | + \\ \diagdown\!-\!N\!-\!(CH_2)_{\overline{m}}\!-\!\text{Urea-like} \\ \quad\quad | \\ RO \quad\quad\quad CH_3 \end{array}$$

The following table provides the name of several representative urea-like cytofectins (alternative names are listed in [ ] below each name), the identities of the lipophilic chains (R), the value of m, and the identity of the urea-like group in each compound.

---

GTU-DMRIE: R—$C_{14}H_{29}$, m = 3 Urea-like = [DMRIE-γ-thiourea]

$$-N(H)-C(=S)-NH_2$$

Glucose-GTU-DMRIE: R—$C_{14}H_{29}$, m = 3 Urea-like = [γ-aminopropyl-DMRIE, α-glucosyl-thiourea]

$$-N(H)-C(=S)-N(H)-\text{1-alpha-glucose}$$

Galactose-GTU-DMRIE: R—$C_{14}H_{29}$, m = 3 Urea-like = [γ-aminopropyl-DMRIE, α-galactosyl-thiourea]

$$-N(H)-C(=S)-N(H)-\text{1-alpha-galactose}$$

Arabinose-GTU-DMRIE: R—$C_{14}H_{29}$, m = 3 Urea-like = [γ-aminopropyl-DMRIE, α-arabonosyl-thiourea]
Arabinose-GTU-DMRIE: R—$C_{12}H_{25}$, m = 3 Urea-like = [γ-aminopropyl-DMRIE, α-arabonosyl-thiourea]

$$-N(H)-C(=S)-N(H)-\text{1-alpha-arabinose}$$

Lactose-GTU-DMRIE: R—$C_{14}H_{29}$, m = 3 Urea-like = [γ-aminopropyl-DMRIE, α-lactosyl-thiourea]
Lactose-GTU-DMRIE: R—$C_{12}H_{25}$, m = 3 Urea-like = [γ-aminopropyl-DMRIE, α-lactosyl-thiourea]

$$-N(H)-C(=S)-N(H)-\text{1-alpha-lactose}$$

AMBOMe-δU-DMRIE: R—C₁₄H₂₉, m = 3 Urea-like =
[δ-aminobutyl-DMRIE, AMBOMe Urea]

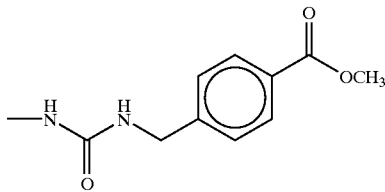

AMBOMe-δU-DMRIE: R—C₁₄H₂₉, m = 3 Urea-like =
[δ-aminobutyl-DMRIE, AMBP Urea]

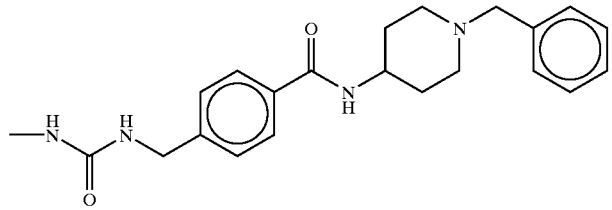

Lys(OMe)-GU-DMRIE: R—C₁₄H₂₉, m = 3 Urea-like =
[γ-aminopropyl-DMRIE, Lysine Methyl Ester Urea]

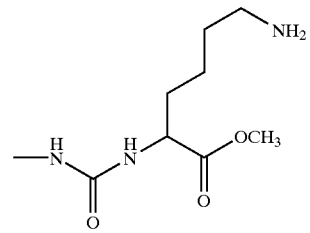

Arg(OMe)-GU-DMRIE: R—C₁₄H₂₉, m = 3 Urea-like =
[γ-aminopropyl-DMRIE, Arginine Methyl Ester Urea]

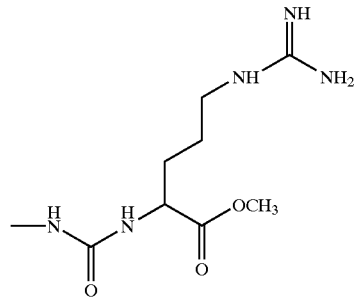

In the above listing, AMBOMe is an abbreviation for 4-aminomethylene benzoic acid methyl ester and AMBP is an abbreviation for 4-aminomethylene benzoic acid 4-amino [N-benzyl] piperidine amide.

4. N⁺-heteroethylene Substituted Cytofectins

The invention also includes another major species of cationic lipids comprising a heteroethylene substitution on the quaternary ammonium of a propaminium group including the β-hydroxyethylene substitution that is characteristic of the RI species of cationic lipid, as well as comprising the amine derivative disclosed in Wheeler et al., Biochem. Biophys. Acta, 1280: 1–11 (1996). This group of compounds includes compounds of the following structure:

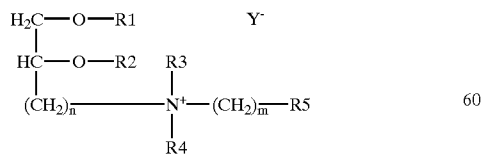

wherein $R_1$ and $R_2$ are independently H, linear or branched, unsubstituted or substituted $C_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—(CH₂)$_k$—CH₃, S—(CH₂)$_k$—CH₃, X—(CH₂)$_k$—, wherein X is a halide, and —N((CH₂)$_k$—CH₃)₂, wherein the alkyl groups of said substituents comprise from 0 to 2 heteroatoms is 0–4, n is 1–6, and m is 2–10; and $R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—(CH₂)$_k$—CH₃, —S—(CH₂)$_k$—CH₃, X—(CH₂)$_k$—, wherein X is a halide, and —N((CH₂)$_k$—CH₃)₂, wherein the alkyl groups of said substituents comprise from 0 to 2 heteroatoms and k is 0–4;

wherein $R_5$ is —O—$R_6$ such that $R_5$—O—$R_6$ comprises an ether linkage, wherein $R_6$ is selected from the group consisting of amino acids, peptides, polypeptides, proteins, nucleic acids, nucleotides, polynucleotides, monosaccharides, disaccharides, polysaccharides, bioactive agents, pharmaceutical agents, and linear or branched, unsubstituted or substituted $C_{1-23}$ heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

n is 1 to 6;

m is 1 to 10; and

Y is a pharmaceutically acceptable anion; and wherein $R_1$ and $R_2$ are not both H.

In some embodiments, m is 2–10.

This group of compounds also includes compounds of the structure:

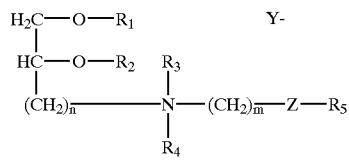

wherein $R_1$ and $R_2$ are independently H, linear or branched, unsubstituted or substituted $C_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

$R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

wherein $R_5$ is selected from the group defined for $R_3$ and $R_4$ and optionally further comprises a chemically linked amino acid, peptide, polypeptide, protein, nucleic acid, nucleotide, polynucleotide, monosaccharide, disaccharide or polysaccharide, or other bioactive or pharmaceutical agent; and Z is NH, or S;

n is 1 to 6;

m is 1 to 10; and

Y is a pharmaceutically acceptable anion;

wherein $R_1$ and $R_2$ are not both H, and wherein if Z is NH and n is 1 and m is 2 to 6, and $R_1$ and $R_2$ separately or together are $C_1$–$C_{23}$ alkyl or C(O)—$C_1$–$C_{23}$, and $R_3$ and $R_4$ separately or together are H or unbranched alkyl $C_1$–$C_6$, then $R_5$ is not —$(CH_2)_z NH2$ where z is 2–6; or —$(CH_2)_3$—NH—$(CH_2)_4$—$NH_2$; or —NH—$(CH_2)_3$—NH—$(CH_2)_4$—NH$(CH_2)_3$—$NH_2$, C(O)-fluorescein, or

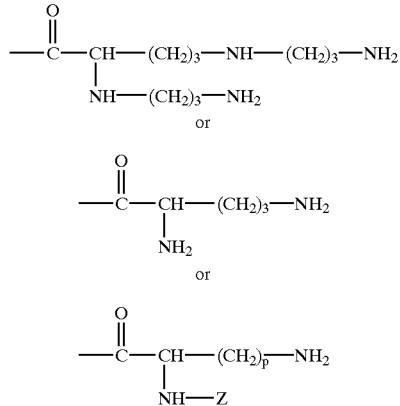

where p is 2–5, Z is H or other groups attached by amide or alkyl amino groups.

In some embodiments, m is 2–10.

In preferred embodiments, the RI lipid moiety is linked to amino acids or polypeptides through an alkyl linker. Alternatively, the cytofectin can include a bifunctional linker, for example hydroxysuccinyl-DORIE-propylamide.

5. Disubstituted RI Cytofectins Having Two Heterosubstituted Groups on the Quaternary Nitrogen Another class of cytofectins of the present invention are the disubstituted RI cytofectins having two heterosubstituted groups on the quaternary nitrogen. This class of cytofectins has the general structure:

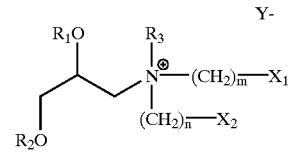

wherein $R_1$ and $R_2$ are independently H, linear or branched, unsubstituted or substituted $C_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0 to 4;

R3 is a linear or branched, unsubstituted or substituted $C_{1-23}$ alkyl, alkylene or heteroalkyl group having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0 to 4;

$X_1$ and $X_2$ are independently selected from the group consisting of $NR_4R_5$ and $OR_4$, wherein $R_4$ and $R_5$ are selected from the group consisting of $R_1$ as defined above, amino acids, peptides, polypeptides, proteins, nucleic acids, nucleotides, polynucleotides, monosaccharides, disaccharides, polysaccharide, other bioactive agents and other pharmaceutical agents;

n is 1 to 8;

m is 1 to 8;

wherein $R_1$ and $R_2$ are not both H.

Preferably, $R_1$ and $R_2$ are saturated or unsaturated $C_{10}$–$C_{18}$ alkyl groups. In another embodiment $R_1$ and $R_2$ are identical and are selected from the group consisting of $C_{14}H_{29}$ and $C_{12}H_{25}$. In a further embodiment, $R_3$ and $R_4$ are selected from the group consisting of $C_1$–$C_5$ alkyl groups and $C_1$–$C_5$ heteroalkyl groups having one heteroatom therein. In yet another embodiment, $R_3$ and $R_4$ are methyl groups. In an additional embodiment, $X_1$ and $X_2$ are $NR_4R_5$ and $R_4$ and $R_5$ are H. In another embodiment, n and m are 2–5.

Representative cytofectins of this class include the compounds listed below. In these compounds, $R_3$ is $CH_3$.

| NAME | STRUCTURE |
|---|---|
| EAPA DLRIE | $R_1 = R_2 = C_{12}H_{25}$ n = 2 m = 3 $X_1 = X_2 = NH_2$ |
| EABA DLRIE | $R_1 = R_2 = C_{12}H_{25}$ n = 2 m = 4 $X_1 = X_2 = NH_2$ |
| BPA DLRIE | $R_1 = R_2 = C_{12}H_{25}$ n = m = 3 $X_1 = X_2 = NH_2$ |
| PABA DLRIE | $R_1 = R_2 = C_{12}H_{25}$ n = 3 m = 4 $X_1 = X_2 = NH_2$ |
| EAFA DLRIE | $R_1 = R_2 = C_{12}H_{25}$ n = 3 m = 5 $X_1 = X_2 = NH_2$ |
| BPA DMRIE | $R_1 = R_2 = C_{14}H_{29}$ n = m = 3 $X_1 = X_2 = NH_2$ |
| PABA DMRIE | $R_1 = R_2 = C_{14}H_{29}$ n = 3 m = 4 $X_1 = X_2 = NH_2$ |
| PAFA DMRIE | $R_1 = R_2 = C_{14}H_{29}$ n = 3 m = 5 $X_1 = X_2 = NH_2$ |

6. Ether Cytofectins

Another class of cytofectins of the present invention are ether cytofectins. These compounds have the general formula:

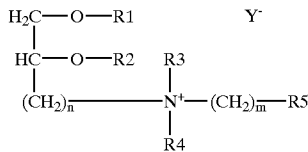

wherein $R_1$ and $R_2$ are independently H, linear or branched, unsubstituted or substituted $C_{1-23}$ alkyl, acyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms k is 0–4, and $R_3$ and $R_4$ are independently linear or branched, unsubstituted or substituted $C_{1-23}$ alkyl, alkylene or heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

wherein $R_5$ is —O—$R_6$ such that $R_5$—O—$R_6$ comprises an ether linkage, wherein $R_6$ is selected from the group consisting of amino acids, peptides, polypeptides, proteins, nucleic acids, nucleotides, polynucleotides, monosaccharides, disaccharides, polysaccharides, bioactive agents, pharmaceutical agents, and linear or branched, unsubstituted or substituted $C_{1-23}$ heteroalkyl groups having from 0 to 6 sites of unsaturation, cyclic and aryl groups, said groups comprising from 0 to 5 heteroatoms wherein said heteroatoms are not the first atoms in said groups, wherein the substituent groups are selected from —O—$(CH_2)_k$—$CH_3$, —S—$(CH_2)_k$—$CH_3$, X—$(CH_2)_k$—, wherein X is a halide, and —N$((CH_2)_k$—$CH_3)_2$, wherein the alkyl groups of said substituents comprise from 0 to 2 heteroatoms and k is 0–4;

n is 1 to 6;

m is 1 to 10; and

Y is a pharmaceutically acceptable anion; and wherein $R_1$ and $R_2$ are not both H.

In some embodiments, m is 2–10.

Bioactive Headgroups on the Cytofectins (a) Targeting Species

A cytofectin according to the present invention can include a molecular species having a biological cell targeting activity as a terminal group. Within this class are cytofectins comprising cell receptor-specific molecules. The receptor-specific peptides or amino acids are typically linked as amides via DMRIE-OX and gAP-DMRIE. Examples of preferred species of this type are DMRIE carboxylate (methionine-leucine-phenylalanine methyl ester)amide (DOx-Met-Leu-Phe-OMe), and pGlu-Pro-His-g-DMRIE, comprising chemotactic peptides. Other ligands for cell surface receptors that can be attached to cytofectins of the invention comprise peptidomimetic analogs; many viral attachment and internalization peptides, lactose and other di- and polysaccharides; acetylcholine analogs; and folic acid derivatives.

A representative targeting compound is AMBP-δU-DMRIE, the structure of which is disclosed above. The AMBP moiety targets the $\sigma_1$ receptor, which is overexpressed in several types of tumors. (See Christy S. John et al., Cancer Research 55:3022–3027 (1995) and Bertold J. vilner et al., Cancer Research 55: 408–413 (1995), the disclosures of which are incorporated herein by reference).

(b) Therapeutic Agents

A cytofectin according to the invention can include as a terminal group a bioactive molecular species. An example of a preferred species of this type is pGlutamate-histidine-proline-γ-DMRIE amide, comprising a thyrotropin-releasing hormone.

(c) Cellular and Intracellular Targeting

A cytofectin according to the invention can comprise a terminal group bearing a ligand that can specifically bind to a cell membrane or intracellular target to effect a desired physiological response. Appropriate ligands may comprise peptides that are viral epitopes, hormones, enzyme substrates, monosaccharides, disaccharides, oligosaccharides, carbohydrates, cofactors, drugs, lectins, oligonucleotides, and nucleic acids. Preferred species among this group are cytofectins comprising chloroquine and other lysosomotropic agents, nuclear localization peptides, corticosteroids and viral peptides or proteins.

Groups Influencing Transfection Efficiency

The cytofectins of the present invention may be linked to groups which influence their transfection efficiencies. Such groups may be amino acids, peptides, polypeptides, proteins, nucleic acids, nucleotides, polynucleotides, mono, di- or polysaccharides. Additionally, the amino acids, peptides, polypeptides, or proteins may include unusual or modified amino acids not generally found in living organisms. Such unusual or modified amino acids include but are not limited to the modified and unusual amino acids listed in 37 C.F.R §1.822. In addition, such amino acids may be synthetic amino acids not found in nature.

Transfection Efficacy

Representative compounds of each class in the DMRIE series together with a measurement of cytofectin activity relative to DMRIE are listed in Table I. Table I clearly demonstrates that DMRIE derivatives having several of the linking groups of the present invention provide efficient levels of transfection.

I: Summary of Cytofectin Headgroup Alterations and Activity

| | | | Activity | |
|---|---|---|---|---|
| Functional Group | Alkyl Link | Name | Cos7 | C2C12 |
| Methyl Ureas | ethyl (C2) | BMU | ≥ | ≤ |
| | propyl (C3) | GMU | ≥ | ≈ |
| | butyl (C4) | DMU | ≫ | ≥ |
| Methyl Carbamates | ethyl (C2) | βMC | ≈ | ≈ |
| | propyl (C3) | γMC | ≈ | ≈ |
| | butyl (C4) | δMC | ≈ | ≈ |
| Sugar-thiourea | | | | |
| glucose | propyl (C3) | Glc-TU-DMRIE | ≥ | ≤ |
| arabinose | propyl (C3) | Ara-TU-DMRIE | ≈ | < |
| galactose | propyl (C3) | Gal-TU-DMRIE | ≥ | ≈ |
| lactose | propyl (C3) | Lac-TU-DMRIE | ND | ND |
| Single Amino Acids | | | | |
| serine | butyl (C4) | δ-ser-DMRIE | ≈ | ≤ |
| methionine | methylene (C1) | DOx-Met-OMe | ≪ | < |
| Peptides | | | | |
| Met-Leu-Phe | methylene (C1) | DOX-MLF-OMe | ≈ | < |
| pGlu-His-Pro | propyl (C3) | TRH-γ-DMRIE | ≈ | ≪ |

Reaction Schemes and Preparation Methods

A. Synthesis of Cytofectins

The compounds of the invention may be prepared by any convenient process. In order to expediently enable the synthesis of the cytofectins of the invention from the key intermediates of Scheme II, generalized methods for the synthesis of these derivatives are presented diagrammatically and in terms of specific examples. The various carboxy cytofectins, both of the carbamyl cytofectin species, and the cytofectins with urea-like functional groups can be prepared according to the synthesis procedures outlined in Schemes III, IV, and V, respectively. The disubstituted RI cytofectins having two heterosubstituted groups on the quaternary nitrogen can be synthesized according to the procedures provided in Scheme VI.

The cytofectins of the invention are conveniently prepared from homologs of a key intermediate having the general formula Compound I-1

Preferred cytofectins wherein n is 1 and m is 2 are prepared from the Compound I-3 of Scheme I, wherein n is 1. Compound I-3 can be prepared from I-1 by alkylation at the hydroxyls of dialkylaminopropanediolto generate I-2 followed by alkylation of N with an R-substituted ethyl group as shown.

Scheme II sets forth a general method of synthesis of the starting compounds for Scheme I for species wherein n=1–6. Various compounds along the route of synthesis are commercially available, for example as the hydroxy-olefin II-3 or the bromo-olefin II-4. Only the cytofectin species wherein n=5 requires starting from the acid II-1. For the preparation of the preferred species wherein n is 1 and m is 2, the final dimethylaminopropanediol is commercially available (Cat. No. 21,021-8, Aldrich Chemical Co., St. Louis, Mo.).

The cytofectins of the invention are prepared by appending various known molecules with reactive functional groups in an appropriate order to the skeleton structure of the key intermediates. The various known compounds, for example, substituted alkyl amines, sugars, ureas, thioureas, amino acids, and peptides are available from commercial sources. Methods for coupling the various functional groups to the key intermediates are well known to those skilled in the art and described in detail in the literature, for example in the monograph series, Reagents for Organic Synthesis Vol. 1–16, John Wiley & Sons, New York, N.Y.

Summary of Synthetic Transformations

Cytofectins of the type claimed in this application may be prepared using conventional synthetic chemistry. The synthetic procedures for all of the cytofectins disclosed herein is essentially the same, but employ different amino-alcohols as starting materials. The skeleton is formed by elaboration of dihydroxy-dialkylamine compounds as illustrated in Scheme I. The hydroxyl functions are linked to hydrophobic alkyl chains using reagents and conditions dictated by the specific substituents desired to be introduced. For example, simple n-alkyl chains may be conveniently introduced by coupling the requisite alkyl methane sulfonate with the alcohols using base catalysis. The tertiary amine is then treated with a functionalized, suitably protected alkylating agent to effect quaternization of the nitrogen. Specific functionalities appended via the quaternary nitrogen may then be elaborated into the various functional classes called Carboxy-, Carbamyl-, and Urea-Cytofectins, as shown in Schemes III, IV, and V. General synthetic strategies such as those disclosed in U.S. Pat. No. 5,334,761, which is incorporated herein by reference, can be used to advantage in the present invention.

To prepare Carboxy Cytofectins according to Scheme III, a primary alcohol moiety linked to the quaternary nitrogen (III-1) is oxidized to the corresponding carboxylic acid (III-2). Numerous reagents may effect this transformation, and we standardly employ a modified chromium trioxide oxidation. The cytofectin carboxylate is typical in that it may be coupled with a variety of alcohols, thiols, and amines to afford the corresponding esters, thioesters, and amides, respectively. In this manner, any material bearing an appropriate nucleophile may be linked to the "basic" carboxy cytofectin skeleton to generate compounds such as III-3 and III-4. For example, the preparation of DMRIE carboxylate propyl amide was effected by DCC-catalyzed coupling of propyl amine with DMRIE carboxylate. The corresponding amino acid and peptide derivatives were prepared using similar technology, and provide further specific illustrations of this type of synthetic route and its application in incorporating biologically active moieties.

Two "orientations" are possible when preparing Carbamyl Cytofectins, and synthetic routes for both orientations are illustrated in Scheme IV. Alcohol moieties appended to the quaternary nitrogen (IVA-1) may be converted to the corresponding carbamates (IVA-2) in several ways, including treatment with an appropriate isocyanate. Amine substituents appended to the quaternary nitrogen (IVB-1) may also be converted to carbamates (IVB-2) in an analogous manner, although different reagents are typically required. For example, the preparation of the methyl carbamate of DMRIE employed coupling the parent cytofectin alcohol with methylisocyanate.

The Urea Cytofectins (V-2) may be prepared from cytofectins bearing a primary or secondary amine function (V-1) according to Scheme V. This may be done in several ways. For example, we have employed both single step conversions using various isocyanates and two step conversions comprised of initial treatment with phosgene followed by coupling with an amine. The preferred methodology for any given compound depends on the functional groups within the starting cytofectin and those present on the amine substituents. For example, γ-amino propyl DMRIE may be treated with methylisocyanate to yield the corresponding methyl urea in one step. Alternately, the two step conversion technique was employed to generate the γ-amino propyl DMRIE arginine methyl ester urea.

Following these generalized procedures, the following cytofectins were among those prepared and tested for transfective activity:

1. RI cytofectins
   Serine-δ-DMRIE amide
   Aspartate-γ-DMRIE amide
   pGlutamate-histidine-proline-γ-DMRIE amide
   (a thyrotropin releasing hormone derivative
   Hydroxysuccinyl-DORIEPropyl Amide
2. Carboxy Cytofectins
   DORIE Carboxylate [C18:1 alkenyl side chains]
   DMRIE Carboxylate [C14 alkyl side chains]
   DMRIE Carboxylate Propyl Amide
   DMRIE Carboxylate(methionine-methyl ester)amide
   DMRIE Carboxylate(methionine-leucine-methylester) amide
   DMRIE Carboxylate(methionine-leucine-phenyl alanine methyl ester)amide [a chemotactic peptide derivative]
3. Carbamyl Cytofectins
   DMRIE Methyl carbamate
   Hydroxypropyl DMRIE Methyl Carbamate
   Hydroxybutyl DMRIE Methyl Carbamate
4. Urea-like Cytofectins
   Ureas
     β-aminoethyl-DMRIE,Methyl Urea
     γ-aminopropyl-DMRIE,Methyl Urea
     δ-aminobutyl DMRIE,Methyl Urea
     γ-aminopropyl-DMRIE,Arginine-Methyl Ester Urea
     γ-aminopropyl-DMRIE,Lysine Methyl Ester Urea
     γ-aminopropyl-DMRIE,Lysine Inner Salt Urea
   Thioureas
     γ-aminopropyl-DMRIE,α-glucosyl thiourea
     γ-aminopropyl-DMRIE,α-galactosyl thiourea
     γ-aminopropyl-DMRIE,α-arabonysl thiourea
     γ-aminopropyl-DMRIE,α-lactosyl thiourea
     DMRIE-γ-thiourea Synthesis of Disubstituted Cytofectins Having Two Heterosubstituted Groups on the Quaternary Nitrogen The synthesis of PABA-DMRIE, a representative disubstituted cytofectin having two heterosubstituted groups on the quaternary nitrogen, is described below.

A solution N-Methyl,N-benzyl amino-2,3-propanediol (3.5 gr) in tetrahydrofuran (105 mL) was alkylated by sequential treatment with sodium hydride (60% in mineral oil, 1.65 gr) then tetradecyl methanesulfonate (10.3 gr) at reflux for 3 days. The reaction was filtered through Celite, evaporated then partitioned between dilute sodium hydroxide (100 mL) and ether (250 mL). The crude product was obtained by drying the solution, then evaporating the ether. Chromatographic purification (silica G, hexane:ethyl ether) afforded the pure dimyristyl ether (6.67 gr, 64%). The benzyl group was removed by catalytic hydrogenation (Pd(OH)$_2$, 0.6 gr) in 140 mL hexane:ethanol (1:1) at low pressure (≈2–3 atm) and ambient temperature. The reaction was periodically monitored by TLC (silica G, chloroform:methanol) and the hydrogen reservoir replenished until the reaction was judged complete. The pure product "DMP-MA" (3.5 gr, 62%) was isolated after chromatographic purification (silica G, chloroform:methanol). Alkylation of DMP-MA (5.0 gr) was effected with 3-bromporopyl-phthalamide (5.4 gr) in ethanol (100 mL) using triethyl amine (7.4 mL) as base catalyst at reflux for 48 hrs. Subsequent to evaporation of solvent and excess volatile reagents, chromatographic purification (silica G, hexane:ether) afforded the desired tertiary amine (4.7 gr, 68%). The bis-phthalimide was prepared by quaternization of the alkoxypropyl, methyl, phthalylpropyl amine (1.5 gr) with 4-brompbutylphthalimide (1.24 gr) using a catalytic amount of potassium iodide (55 mg) in dimethylformamide (5 mL) at 95° C. overnight. Subsequent to evaporation of the dimethylformamide, the pure quaternary bis-phthalimide product (1.18 gr, 55%) was isolated after chromatographic purification (silica G, chloroform:methanol). Simultaneous deprotection of the two masked primary amines in the bis-phthalimide (1.1 gr) was accomplished by treatment with anhydrous hydrazine (0.7 mL) in absolute ethanol (25 mL) overnight. The reaction was diluted with 150 mL chloroform and the phthalhydrazide by-product removed by filtration. After evaporating the filtrate, the residue was partitioned between 65 mL chloroform, 24 mL methanol and 24 mL of 0.1 N sodium hydroxide. The organic layer was dried with sodium sulfate, filtered and evaporated. Extensive high vacuum treatment afforded the desired product as a waxy low melting solid (0.55 g, 68%) which was >95% homogenous based on proton NMR and TLC.

A scheme illustrating the synthesis of PABA-DMRIE is provided in Scheme VI.

The PABA DMRIE synthesis described above illustrates the general route to the disubstituted cytofectins and highlights the ability to sequentially incorporate the two heterosubstituted groups on the quaternary nitrogen. This feature allows the ready introduction of diverse substituents. Thus, using bromoethanol in lieu of 4-bromobutylphthalimide in the quaternization step, followed by deprotection as described would afford one amine and one alcohol moiety in the final product. Alternatively, compounds having two alcohol moieties linked to the quaternary nitrogen may be synthesized by substituting a bromoalcohol for the bromophthalimide at either condensation step. Additional disubstituted RI cytofectins having two hetero substituted groups on the quaternary nitrogen may be prepared using the above procedures in combination with conventional synthetic methodologies.

Synthesis of Ether Cytofectins

Ether type cytofections may be readily prepared using standard chemical techniques. Ether linkages may be introduced into an hydroxyl bearing cytofectin containing a quaternary ammonium group by using the alcohol as a nucleophile. Alternatively, electrophilic compounds which contain ether linkages may be condensed with an appropriate lipophilic tertiary amine in a quatranization reaction to produce a cytofectin. Thus, DMRIE methyl ether could be prepared by reacting DMRIE with methyl iodide under base catalysis, or by condensing the tertiary amine precursor to DMRIE (N,N-dimethyl-2,3-ditetradecyloxy-propane) with 2-bromoethyl-methyl ether. More complicated ether derivatives may also be prepared. For instance, an alcohol bearing cytofectin such as butyl-DMRIE can be condensed with per-acetylated alpha-bromo-mannose to afford the per-acetyl saccharide. Deacetylation affords the anticipated mannose derivatized cytofectin wherein the sugar is linked by ether linkage. Similarly, treatment of butyl-DMRIE with dihydropyran and catalytic acid should afford the corresponding DHP ether. Condensation of DMRIE with bromo ethyl acetate would afford the 2-carbethoxyethyl ether of DMRIE.

The preparation of other compounds claimed herein is within the ability of those skilled in the art. For example, to make compounds having a secondary amine on the quaternary nitrogen, a primary amine may be alkylated using the procedures described in the synthesis of PABA-DMRIE provided herein.

The methods described above may be used to prepare a large number of cytofectins for screening in a reasonable period of time. Synthesis in conjunction with screening can be used to efficiently select the most effective cytofectin for a defined application.

It is generally known to one skilled in the art that in the case of molecules having more than one reactive functional group, it is necessary to block or mask one or more of those groups which are not intended to participate in the particular coupling reaction.

Formulations

The compounds of the invention can be used in formulations to transfect mammalian cells both in vitro and in vivo. Formulations for transfection are known to those skilled in the art and are disclosed, together with methods for their preparation, for example, in U.S. Pat. No. 5,264,618 to Felgner, U.S. Pat. No. 5,334,761 to Gebeyehu et al, and Felgner et al. (*J. Biol. Chem.* 269:2550–2561, 1994), which are hereby incorporated by reference. The cationic lipids of the invention can be combined with amphipathic lipids such as phospholipids and with neutral lipids, such as cholesterol to form lipid vesicles, which can be liposomes, unilammelar vesicles, micelles, or simple films.

Cationic lipids of the invention are particularly useful in facilitating gene therapy, as disclosed in clinical trials reported by Nabel et al. (*Human Gene Therapy* 3:399–410, 1992). The use of cationic liposomes is known to be useful for facilitating entry of polynucleotides, macromolecules, and small molecules into cells of the blood vessels, the systemic circulation, lung epithelial cells, brain tissue and frog embryos (Xenopus).

It is also noted that the cytofectins of the present invention are useful in transfecting cells in vitro. Although various compounds within the scope of the present invention are somewhat tissue specific in vivo, most or all are useful for transfection of cultured cells in vitro. For any particular candidate cytofectin of the present invention, its relative transfection efficacy in vitro and in various tissues in vivo can be readily ascertained using screening assays such as those disclosed in Examples 8–14.

Experimental Procedures

The chemical reactions described below are disclosed in terms of their general application to the preparation of the cationic lipids of the invention. Occasionally, the reaction may not be applicable as described to each molecular species within the disclosed scope. The compounds for which this occurs will be readily recognized by those skilled in the art. In all such cases, either the reactions can be successfully performed by conventional modifications known to those skilled in the art, that is, by changing to alternative conventional reagents, or by routine modification of reaction conditions. Alternatively, other reactions disclosed herein or otherwise conventional will be applicable to the preparation of the compounds of the invention. In all preparative methods, all starting materials are known or readily preparable from known starting materials.

The present invention is described below in detail using the following examples, but the methods disclosed are applicable for the preparation of all cationic lipids covered by the scope of the invention and are not limited to the examples. All of the temperatures indicated in the Examples are in degrees Celsius and are uncorrected.

EXAMPLE 1

Preparation of a Carboxy cytofectin: DMRIE-Ox

DMRIE Br (1.14 g) is dissolved in 18 mL dimethylformamide with gentle stirring, then 2.71 g pyridinium dichromate is added and the reaction vessel is purged thoroughly with argon and tightly stoppered. After 18 h the solvent is removed at reduced pressure. The residue is partitioned between ethyl ether and 0.2N sodium hydroxide. The organic layer is collected and the aqueous layer is extracted repeatedly with ether. The combined organic extracts are dried with $MgSO_4$, then filtered and evaporated to afford crude product. Chromatography through silica gel with $CHCl_3$; $MeOH:NH_4OH:H_2O$ (90:10:0.25:0.25)affords pure product.

EXAMPLE 1A: DPRIE carboxylate; and EXAMPLE 1B: DORIE carboxylate were prepared following the procedure described in Example 1, using DPRIE Br and DORIE Br, respectively, as starting materials in place of DMRIE Br.

EXAMPLE 2

Preparation of a Carboxy Cytofectin Ester: DMRIE-Ox Ethyl Ester

The carboxy cytofectin product of Example 1, DMRIE-Ox, (300 mg) was dissolved in 7 mL chloroform and washed with 3 mL 1N HCl. The organic phase was dried with $MgSO_4$, then filtered into a reaction vessel. Anhydrous ethanol (100 mL) and dicyclohexylcarbodiimide(1.3 mL of a 0.5 M solution in dichloromethane) were added, the flask was then stoppered and stirred overnight at ambient temperature. The reaction was filtered through a medium glass frit to remove any solid byproducts, then evaporated. Chromatography of the evaporation residue using silica gel with $CHCl_3:MeOH:NH_4OH:H_2O$ (90:10:0.25:0.25)afforded pure product.

EXAMPLE 3
Preparation of a Carboxy Cytofectin Amide: DMRIE-Ox Propyl Amide

DMRIE-Ox (300 mg) was dissolved in 7 mL chloroform and washed with 3 mL 1N HCl. The organic phase was dried with $MgSO_4$, then filtered into a reaction vessel. The solution was placed in an ice-water bath and N-hydrosuccinimide (82 mg) then dicyclohexylcarbodiimide(1.3 mL of a 0.5 M solution in dichloromethane) were added and the reaction was allowed to stir with warming for 8 hours. At this time propyl amine (40 mg) was added as a neat liquid and the reaction allowed to stir at room temperature overnight. The reaction was filtered, then evaporated. Chromatography of the filtrate residue through silica gel with $CHCl_3$:MeOH:$NH_4OH$:$H_2O$ (90:10:0.25:0.25) afforded pure product.

EXAMPLE 3A: DMRIE carboxylate(methionine-methyl ester)amide; EXAMPLE 3B: DMRIE carboxylate (methionine-leucine-methyl ester)amide; and EXAMPLE 3C: DMRIE carboxylate(methionine-leucine-phenyl-alanine-methylester)amide were prepared in a similar procedure by substitution of the corresponding amines for propyl amine in the protocol of Example 3.

EXAMPLE 4
Preparation of a Cytofectin Urea: DMRIE-β-Methyl Urea

βAE-DMRIE (1 g) was dissolved in 20 mL dry chloroform with stirring and methylisocyanate(100 mg) was added as a neat liquid. The reaction was stirred overnight then the solvent and excess isocyanate were removed by evaporation. The residue was chromatographed on silica gel with $CHCl_3$:MeOH:$NH_4OH$:$H_2O$ which afforded pure product.

EXAMPLE 4A: γ-aminopropyl-DMRIE, methylurea; and EXAMPLE 4B: γ-aminobutyl-DMRIE, methylurea were prepared similarly by substitution of γ-aminopropyl-DMRIE and γ-aminobutyl-DMRIE, respectively, as starting material.

EXAMPLE 5
Preparation of a Cytofectin Carbamate: DMRIE-β-Methyl Carbamate

DMRIE (1 gm) was dissolved in 15 mL dry chloroform with stirring followed by addition of triethylamine (1.3 mL). Methylisocyanate (100 mg) was then added as a neat liquid, and the reaction was stirred overnight. The reaction was quenched by sequential addition of 20 mL chloroform and 20 mL 0.2N HCl. The biphasic mixture was stirred for approximately 1 h, then transferred to a separatory funnel and the organic phase collected. The solution was dried with magnesium sulfate, filtered, concentrated then treated with high vacuum to give the crude product as a foam. The material was chromatographed with silica gel using elution with $CHCl_3$:MeOH:$NH_4OH$:$H_2O$ (90:10:0.25:0.25) to afford pure product.

EXAMPLE 5A: hydroxypropyl DMRIE methyl carbamate; and EXAMPLE 5B: hydroxybutyl DMRIE methyl carbamate were prepared similarly by substitution of hydroxypropyl DMRIE and hydroxybutyl DMRIE, respectively, as starting material.

EXAMPLE 6
General Scheme for Urea-linked Amino Acids Preparation of DMRIE-γU-Arg($NO_2$)—OMe A dry reaction vessel equipped with magnetic stirring was maintained under an argon atmosphere, then charged with 12 mL dry chloroform and 3.2 mL of 1.93 M phosgene in toluene. The flask was chilled in an ice/water bath and while stirring, a solution containing 1.40 gr γAP DMRIE and 1.2 mL triethylamine in 12 mL dry chloroform was added dropwise over about 5 min. The reaction was stirred at ice/water temperature for 1 hr, then the cold bath removed and the reaction allowed to come to ambient temperature over 2.5 hr. At this time, a warm water bath was used to gently heat the reaction while excess reagents and solvent were removed evaporatively with a stream of dry argon over about 1 hr. The residue was redissolved in 20 mL chloroform and a solution containing 1.20 gr H—Arg($NO_2$)—OMe—HCL and 0.6 mL triethylamine in 7 mL dimethylformamide and 10 mL chloroform was added dropwise at ambient temperature with stirring over 5 min and the reaction allowed to stir overnight under an argon atmosphere. Evaporative removal of the solvent followed by chromatography on silica gel using a chloroform:methanol:aqueous ammonia solvent system afforded 1.47 gr of TLC homogenous product evidencing appropriate NMR, IR, UV and high resolution mass spectra.

EXAMPLE 6A: γ-aminopropyl-DMRIE, Lysine methyl ester urea; and EXAMPLE 6B: γ-aminopropyl-DMRIE, Lysine inner salt urea were prepared similarly by substituting DMRIE-γU-Lys($NO_2$)—OMe and DMRIE-γU-Lys ($NO_2$), respectively, as starting material.

EXAMPLE 7

Intralung Transfection Assay

Adult (4–16 weeks) female BALB/c mice were lightly anesthetized with metophane and 132 μg chloramphenicol acetyltransferase (CAT) DNA±cationic lipid in 100 μl USP saline or water was delivered intranasally using a disposable sterile, plastic insulin syringe fitted with a small plastic catheter. All fluids and syringes were equilibrated to room temperature and the delivery of the single 100 μl volume of DNA required less than one minute. Two or three days post-delivery, the mice were killed by sodium pentobarbital overdose, and the lungs extracted as follows.

Lungs were immediately frozen and stored at −78° C. Frozen lungs were individually pulverized into a fine powder by grinding over 0.4 ml frozen lysis buffer in a 1.5 ml tube using a reversible drill and a bit that just fits into the tube, and the powder is stored in the same tube at −78° C. until extraction. Frozen powders are thawed and 100 μl of Reporter Lysis Buffer from Promega (Catalog #E397A) is added to each. The samples were vortexed for 15 minutes, frozen-thawed three times using alternating liquid nitrogen and room temperature water baths and centrifuged three minutes at 10,000×g. The supernatant was transferred to another 1.5 ml tube and the extraction process repeated (without freeze-thawing) after adding another 500 μl lysis buffer to the pellet. The second supernatant was combined with the first and stored at −78° C.

The cationic lipids used were the DLRIE series (n=2–6) and the DOAP series wherein the alkyl chain has either 10, 12 or 14 carbon atoms. The DOAP series corresponds to formula 2 in which R1=R2=unbranched alkyl chain, n=1, $R_3$=$R_4$=$CH_3$, m=3, G=N and $R_5$=H.

CAT assays were performed by the radioactive partition method of Sankaran (*Anal. Biochem.*, 200:180–186, 1992) or by using a CAT ELISA kit (Boehringer Mannheim, Indianapolis, Ind.). Briefly, CAT tissue homogenates were disrupted by freeze-thawing three times in an ethanol/dry ice bath. Cellular debris was removed by centrifugation and the protein extract was incubated with $^{14}$C-chloramphenicol and acetyl CoA. The chloramphenicol was extracted with ethyl acetate and thin layer chromatography was performed to determine the percent of $^{14}$C-chloramphenicol converted by the extracted cellular protein. Cell extracts were standardized to 2 μg protein incubated for 20 minutes. Tissue extracts were standardized to 200 μg protein incubated for four hours.

Figure 2:
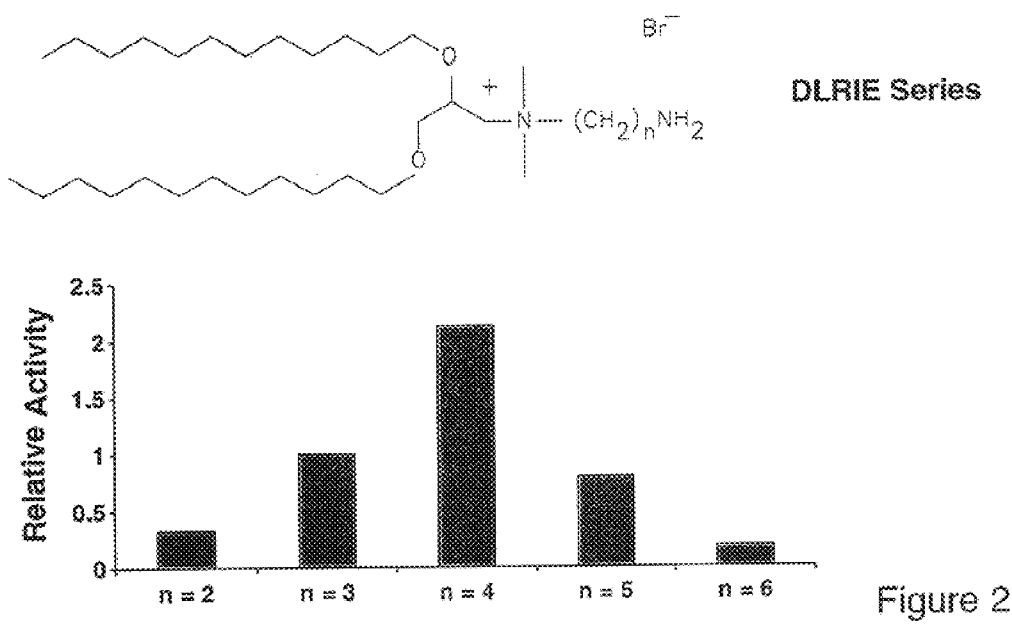
FIG. 2 is a graph of pulmonary expression of CAT in mouse lung when transfection was mediated with cytofectins having alkylamine moieties of differing chain length.
Figure 3:
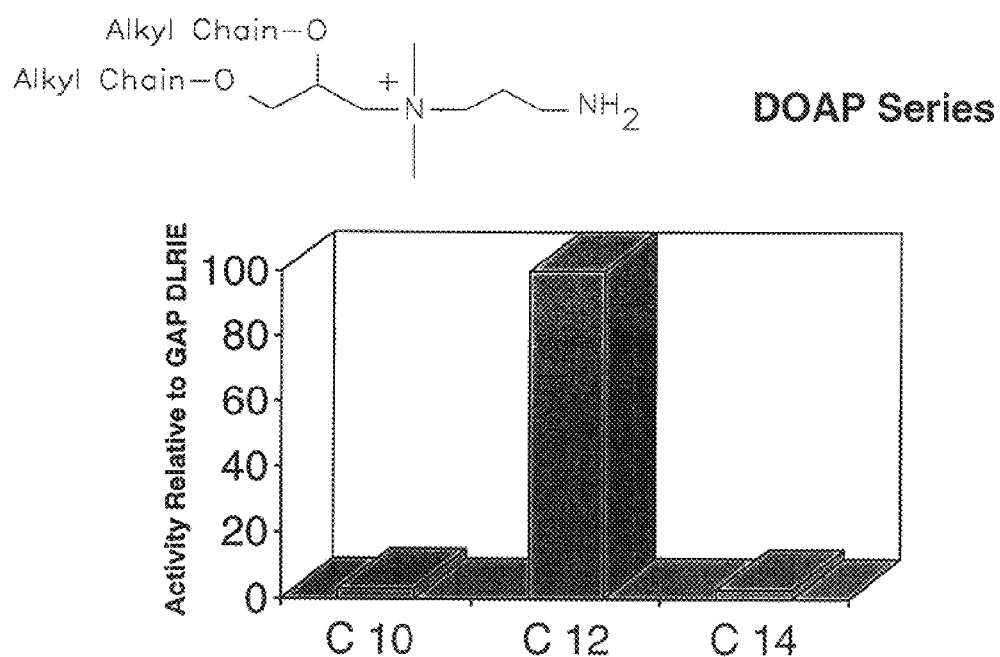
FIG. 3 is a graph of pulmonary expression of CAT in mouse lung when transfection was mediated with cytofectins having alkyl chains of $C_{10-14}$.
Figure 4:
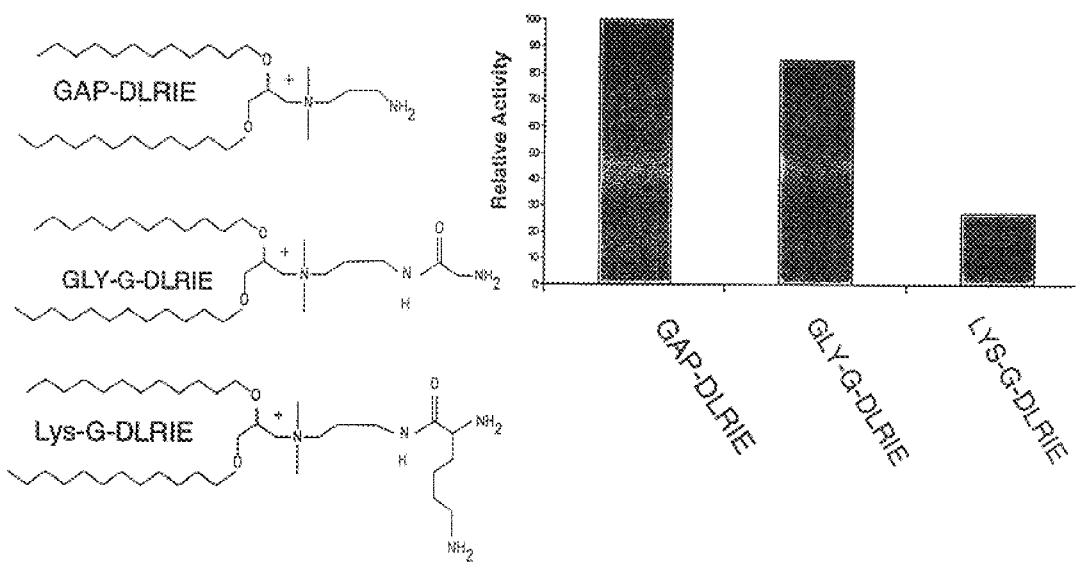
FIG. 4 shows the activities of the amino acid linked compounds Gly-G-DLRIE and Lys-G-DLRIE relative to GAP-DLRIE in the murine lung assay.

Standard curves were constructed using purified enzyme (Sigma, St. Louis, Mo.) spiked into lung extracts or enzyme provided in the ELISA kit. The two CAT assay methods yielded equivalent pg CAT per sample from the same set of extracts. The results are summarized in FIGS. 2 and 3. For the DLRIE series, the most effective distance from the quaternary nitrogen at which to place the primary amine was four carbons (n=4). (FIG. 2). FIG. 3 explores the effect of alkyl chain length on transfection efficiency for the DOAP series, indicating that the C12 compounds are significantly more effective at mediating pulmonary DNA transfection than are the C10 or C14 compounds. FIG. 4 compares the activities of the amino acid linked compounds Gly-G-DLRIE and Lys-G-DLRIE relative to GAP-DLRIE. Gly-G-DLRIE was particularly effective in the murine lung system. FIG. 4 demonstrates that linking an uncharged, non-polar amino acid such as glycine may to the cytofectin core structure may confer a higher level of transfection efficiency than that obtained with a charged, polar amino acid such as lysine.

The tests reported here not only indicate that the compounds of the present invention are active in transfection, but also demonstrate how to select and optimize cytofectins for transfection of particular tissues. Although particular optimum structures are readily apparent for this assay, it will be appreciated that these results are tissue specific; in other words, even cytofectins that performed suboptimally in this assay have valuable activity in other assays, such as in vitro transfection and intraperitoneal transfection.

EXAMPLE 8

Effect of Formulation on in vitro Transfection
Comparison of GMU-DMRIE with DMRIE
Cytofectin:

Solutions of a DMRIE or GMU-DMRIE in chloroform were prepared on a weight to volume (w/v) basis. Aliquots of cationic lipid and neutral lipid (when used) were transferred aseptically to sterile vials in amounts calculated to provide the relative and absolute lipid concentrations desired upon reconstitution with 1 ml of aqueous vehicle. Bulk chloroform was removed with a stream of dry nitrogen, and the vials were treated with high vacuum overnight to remove any residual solvent.

DNA-lipid complexes:

Plasmid DNA at 5 mg/ml of phosphate buffered saline (PBS) as well as the dried, formulated cytofectin-neutral lipid mixture were suspended in OPTIMEM™ (Gibco BRL) and mixed together in 96 well plates at the desired mass/molar ratio as indicated in the Tables. The DNA-lipid complexes were added to the cells within 2 hours after mixing.

Transfection

Cell Lines:

The cell lines used were obtained from the American Type Culture Collection (ATCC, Rockville, Md.) as follows: COS7 monkey kidney cells (ATCC CRL 1651); and C2C12 mouse myoblast muscle cells (ATCC CRL 1772).

All cells were passaged 1:5 to 1:10 in 10% fetal bovine serum (FBS) and Dulbecco's Modified Eagles medium (DMEM). All cells were expanded through 10 doubling passages upon receipt and aliquots were stored frozen. Upon re-expansion, all cells were used for transfection studies before another 10 passages.

Transfection Assays:

On day 0, 20,000 cells in 100 microliters 10% FEBS/90%DMEM were seeded into each well of 96-well culture plates (Nunc) and cultured overnight in a 5% $CO_2$ incubator at 37° C. On Day 1, the medium was aspirated carefully without dislodging cells, and 100 microliters of GMU-DMRIE/pRSV lacZ/DOPE in serum-free OPTIMEM™ (Gibco BRL) was added. DMRIE was used as a reference standard. The lacZ gene encodes the enzyme β-galactosidase which can be assayed colorimetricaly. The cationic lipid-:DOPE ratios varied for each well. After 4 hours of culture, 50 microliters 30% FBS/70% OPTIMEM™ was added to each well. On Day 2, each well received 100 microliters 10%FEBS/90% OPTIMEM™. On Day 3, the medium was removed and 50 microliters lysis buffer (0.1% Triton-X100 in 250 mM Tris, pH 8.0) was added and the plates were stored at 70° C. for at least 20 hours. After thawing, the well media were assayed for their content of β-galactosidase enzyme activity according to Felgner et al. (*J. Biol. Chem.* 269:2550–2561, 1994).

The results (FIGS. 1*a*–1*d*) show that total expression of β-gal in COS7 cells and C2C12 cells was optimal at a GMU-DMRIE/DOPE ratio of 50:50 in both cell lines. Additionally, in COS7 cells a GMU-DMRIE/DOPE ratio of 75:25 was also highly effective. Peak β-gal expression occurred at in COS7 cells at a GMU-DMRIE/DOPE ratio of 75:25 or 50:50. Similar ratios of GMU-DMRIE/DOPE gave peak β-gal activity in C2C12 cells. Total β-gal expression in both cell lines was significantly decreased when the ratio of GMU-DMRIE alone was used. GMU-DMRIE produced higher levels of activity than those achieved by DMRIE in COS7 cells. In C2C12 cells GMU-DMRIE gave significantly higher levels of total activity than DMRIE. The screening assay used in these tests is useful for demonstrating transfection activity and for optimizing the cytofectin/colipid ratio.

EXAMPLE 9

Intraperitoneal Tumor Assay

Two hundred thousand murine B16 tumor cells in 500 μl RPMI were injected intraperitoneally into C57/B16 mice at day 0. At day 7–14, mice received intraperitoneal injections of 0.5 mg CAT DNA in 1.5 ml saline containing cytofectin at a 10:1 molar ratio of cytofectin:DNA. The cationic lipids used were DMRIE, GAP-DMRIE, GAP-DLRIE, and GMU-DLRIE. Two days later, tumors were collected, extracted and assayed for CAT activity as described in Example 7. The CAT activities observed with the cytofectin formulations is compared to a control receiving DNA alone in FIG. 5. Each cationic lipid resulted in significant CAT expression in tumor cells, indicating entry and functional expression of the CAT DNA in the cells. CAT activity was greatest in cells transfected with DMRIE. GAP-DLRIE was nearly as effective as DMRIE while GAP-DLRIE and GAP-DMRIE also exhibited significant activity.

Figure 5:
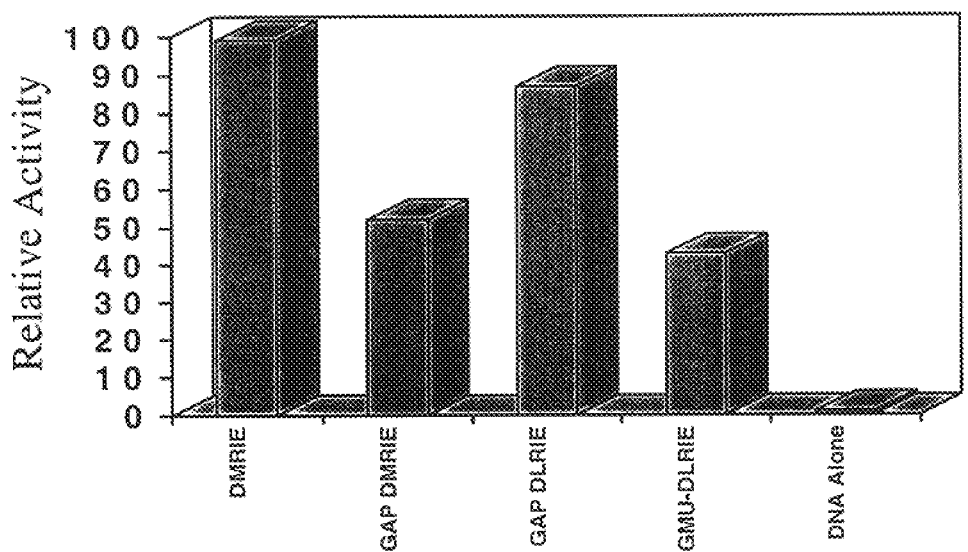
FIG. 5 is a graph comparing intraperitoneal transfection activity of three cytofectins in a mouse tumor model.

FIG. 5 demonstrates that the cytofectins having a primary amine within three carbons of the quaternary nitrogen permit the efficient transfection of DNA in the intraperitoneal tumor assay.

EXAMPLE 10

Intramuscular Assay

The quadriceps of restrained, awake mice are injected with 50 μg luciferase or CAT DNA±cytofectin in 50 μl USP saline using a disposable sterile, plastic insulin syringe fitted with a 28G ½ needle (Becton-Dickinson) and a plastic collar cut from a yellow Eppendorf micropipette tip. The collar length is adjusted to limit the needle orifice penetration to a distance of about 2 mm into the central part of the 3 mm diameter rectus femoris muscle. Injection fluids and syringes are equilibrated to room temperature and injection of the single 50 ml volume of saline-DNA requires several seconds. The entire quadriceps muscle group (140–180 mg wet weight) is collected from each mouse leg at various times post-injection. Muscles are frozen and lysed as described in Example 7.

Luciferase activity is assayed using an automated microplate luminometer (Dynatech Model ML2250). One hundred µl of luciferase substrate is added by the luminometer's injection system to 20 µl extract and sample light units are recorded. The luciferse content of the samples is calculated from Relative light Units using a standard curve of purified firefly luciferase performed in the presence of uninjected muscle extract. The luciferase activity present in the injected muscle extract is much higher than in the uninjected muscle extract.

This assay illustrates another screening assay for optimizing the structure of a particular cytofectin for use in a particular tissue.

EXAMPLE 11

Gene Transfer into Porcine Arteries and Atherosclerotic Rabbit Arteries

Liposome transfection of porcine arteries is performed by anesthesia, intubation and sterile exposure of the iliofemoral arteries as described. (Nabel et al., *Science*, 249:1285–1288, 1990). A double balloon catheter is inserted into the iliofemoral artery, and the proximal balloon is inflated to 500 mm Hg for 5 minutes. The balloon is deflated and the catheter is advanced so that the central space between the proximal and distal balloon is irrigated with heparinized saline. The CAT DNA solution (CAT DNA±cytofectin is instilled for 20 minutes in the central space of the catheter. The catheter is removed and antigrade blood flow is restored. Arteries are analyzed two days later for recombinant CAT expression. Arteries transfected with CAT DNA in the presence of cationic lipid exhibit a significant increase in CAT gene expression compared to arteries contacted with the DNA alone.

In vivo gene transfer of atherosclerotic rabbit iliac arteries is performed using a double injury model which is described by Faxon et al. (*Arteriosclerosis*, 4:189–195, 1984). After the second angioplasty injury is completed, the angioplasty balloon is withdrawn slightly so that the end hold infusion port of the catheter is at the proximal end of the injury. A ligature is placed at the distal end of the injury and the injured segment is flushed with heparinized saline and CAT DNA±cationic lipid liposome solution is instilled for 20 minutes into the isolated injured segment. The catheter is removed and antigrade blood flow is restored. Arteries are analyzed two days later for recombinant CAT expression. Arteries transfected with CAT DNA in the presence of cationic lipid exhibit a significant increase in CAT gene expression compared to arteries contacted with the DNA alone.

EXAMPLE 12

NP Antibody Assay

Transfection of muscles with pDNA encoding a foreign antigen elicits both humoral and cellular immune responses. In order to determine the extent of transfection augmentation in an assay using the humoral immune response as the read-out, changes in the antibody levels subsequent to immunization with naked plasmid DNA (pDNA) encoding an antigen, and the same plasmid DNA complexed with cytofectins, are quantified. The assay is essentially as described by Ulmer et al. (*Science* [1993] 259 1745–1749, the disclosure of which is incorporated herein by reference in its entirety). In the present case Balb/c mice are immunized using pDNA coding for influenza nuclear protein (NP) complexed with cytofectins formulated as a 1:1 (mol:mol) mixture with the co-lipid DOPE (dioleylphosphatidylethanolamine). The cytofectins are routinely screened at a pDNA-phosphate/cytofectin molar ratio of 4:1. Each animal is injected with 5 µgr pDNA in 50 µL physiological saline per leg in the rectus femorus muscle (10 µgr pDNA total per animal) alone or as a cytofectin complex. Complexes are prepared by mixing equivalent volumes of pDNA in saline with cytofectin/co-lipid liposomes also prepared in saline. Injections are at day "0" and at 3 weeks. After 6 weeks total (3 weeks after the boost) serum is removed from the animals and the NP titers are determined by serial dilution using an ELISA assay similar to that reported by Ulmer et al. Data are analyzed based on the ratio of the Geometric Mean Titer (groups of 5 animals) in evidence from a cytofectin augmented transfection versus the titers found using pDNA alone.

Figure 6:
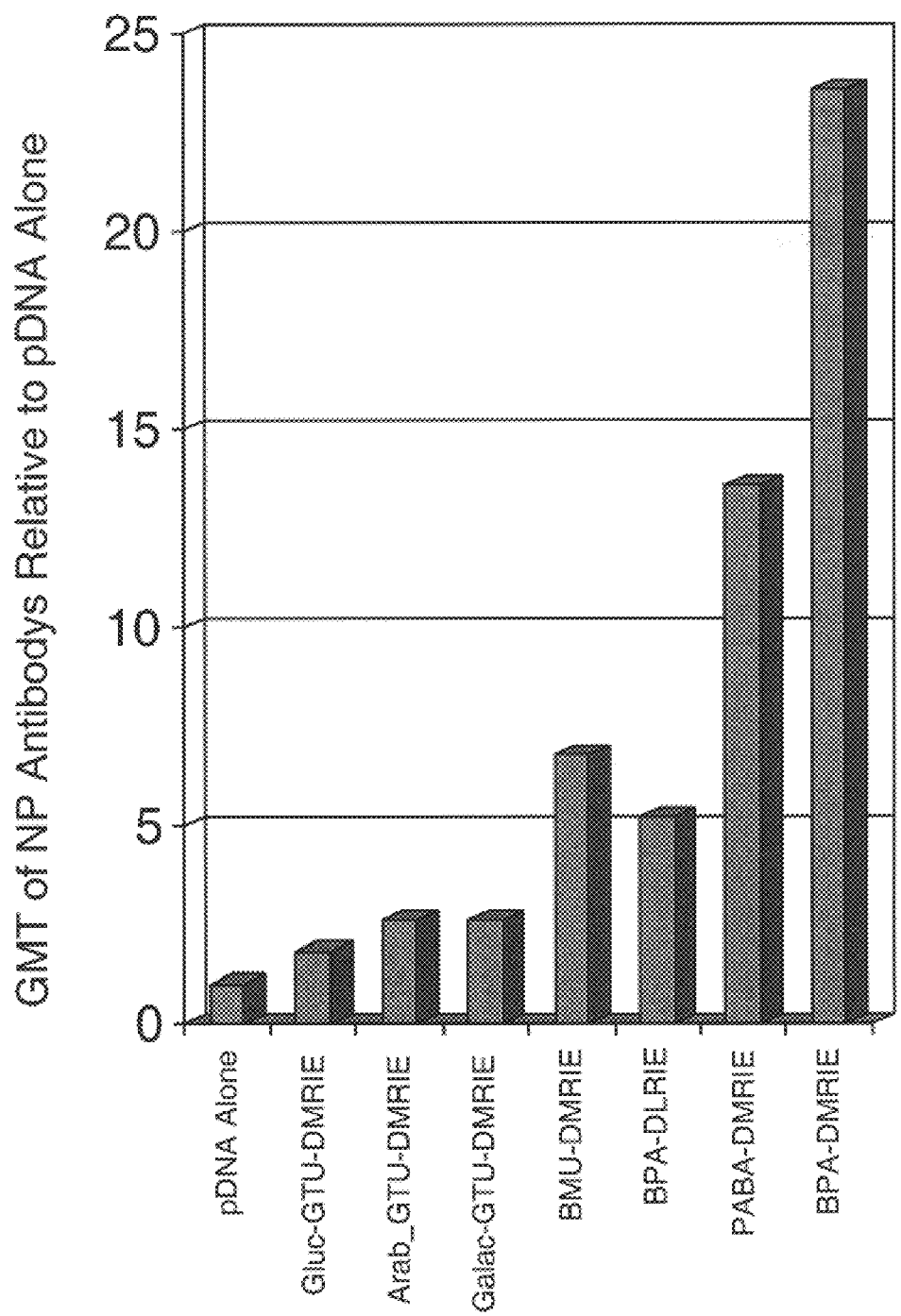
FIG. 6 is a graph of the results of an NP antibody assay comparing the activities of Gluc-GTU-DMRIE, Arab-GTU-DMRIE, Galac-GTU-DMRIE, BMU-DMRIE, BPA-DLRIE, PABA-DMRIE, and BPA-DMRIE with that of DNA alone.

The results of an NP antibody assay using Gluc-GTU-DMRIE, Arab-GTU-DMRIE, Galac-GTU-DMRIE, BMU-DMRIE, BPA-DLRIE, PABA-DMRIE, and BPA-DMRIE are illustrated in FIG. 6. Each of the compounds tested exhibited greater activity than naked DNA alone. BMU-DMRIE, BPA-DLRIE, PABA-DMRIE, and BPA-DMRIE exhibited particularly high activity in this assay.

EXAMPLE 13

General Subcutaneous Tumor Transfection Assay

Tumors are prepared by injecting a suspension of tumor cells subcutaneously on the side of a mouse strain which is compatible with the specific tumor type. The tumors are periodically measured. Once they have reached a size suitable for injection, the tumor volume is approximated based on the measured diameter assuming a spherical tumor. A complex of the cytofectin to be evaluated with a plasmid encoding a reporter gene in a volume of saline equal to the volume of the tumor to be treated is then injected at a flow rate optimized for the particular tumor type. After an appropriate time, the tumors are collected, frozen, then ground up. The reporter gene product is subsequently extracted and the quantity which was expressed is determined using extraction and assay conditions appropriate for the particular gene product being used. A variety of tumor types may be evaluated using this general technique, and different reporter genes are more or less appropriate depending on the tumor type. A specific example of this assay involving melanoma tumors is provided in Example 14 below.

EXAMPLE 14

Subcutaneous Melanoma Tumor Model

BF16F10 melanoma tumors are propagated in 90% RPMI 1640/10% Fetal Bovine Serum. The tumors are injected subcutaneously into the side of BALB/C mice in 75 μL of a suspension containing approximately $10^6$ cells/mL tissue culture medium. When the tumors have reached 4.5 to 7 mm in diameter the volume of each individual tumor is calculated by measuring the diameter of the tumor and assuming a spherical tumor. For each individual tumor, a volume of the cytofectin/CAT plasmid complex in saline equivalent to the calculated volume of the tumor is injected into the tumor at a rate of 2 mL/min. After 48 hours, the tumors are collected, frozen, ground up, and extracted with 1.5 mL of extraction buffer as described in Example 3. CAT activity is quantitated as described below.

Tumors were individually pulverized into a fine powder by grinding over 0.4 ml frozen lysis buffer in a 1.5 ml tube using a reversible drill and a bit that just fits into the tube, and the powder is stored in the same tube at −78° C. until extraction. Frozen powders were thawed and 100 μl Reporter Lysis Buffer from Promega (Catalog #E397A) was added to each. The samples were vortexed for 15 minutes, frozen-thawed three times using alternating liquid nitrogen and room temperature water baths and centrifuged three minutes at 10,000×g. The supernatant was transferred to another 1.5 ml tube and the extraction process repeated (without freeze-thawing) after adding another 500 μl lysis buffer to the pellet. The second supernatant was combined with the first and stored a −78° C.

The cytofectins used were as follows: Gal-GTU-DMRIE, Gluc-GTU-DMRIE, Lac-GTU-DMRIE, Arg(OMe)-GU-DMRIE, AMBP-GU-DMRIE, GTU-DMRIE, and BPA-DMRIE.

CAT assays were performed by the radioactive partition method of Sankaran (*Anal. Biochem.*, 200:180–186, 1992) or by using a CAT ELISA kit (Boehringer Mannheim, Indianapolis, Ind.). Briefly, CAT tissue homogenates were disrupted by freeze-thawing three times in an ethanol/dry ice bath. Cellular debris was removed by centrifugation and the protein extract was incubated with $^{14}$C-chloramphenicol and acetyl CoA. The chloramphenicol was extracted with ethyl acetate and thin layer chromatography was performed to determine the percent of $^{14}$C-chloramphenicol converted by the extracted cellular protein. Cell extracts were standardized to 2 mg protein incubated for 20 minutes. Tissue extracts were standardized to 200 mg protein incubated for four hours.

Standard curves were constructed using purified enzyme (Sigma, St. Louis, Mo.) spiked into lung extracts or enzyme provided in the ELISA kit. The two CAT assay methods yielded equivalent pg CAT per sample from the same set of extracts.

Figure 7:
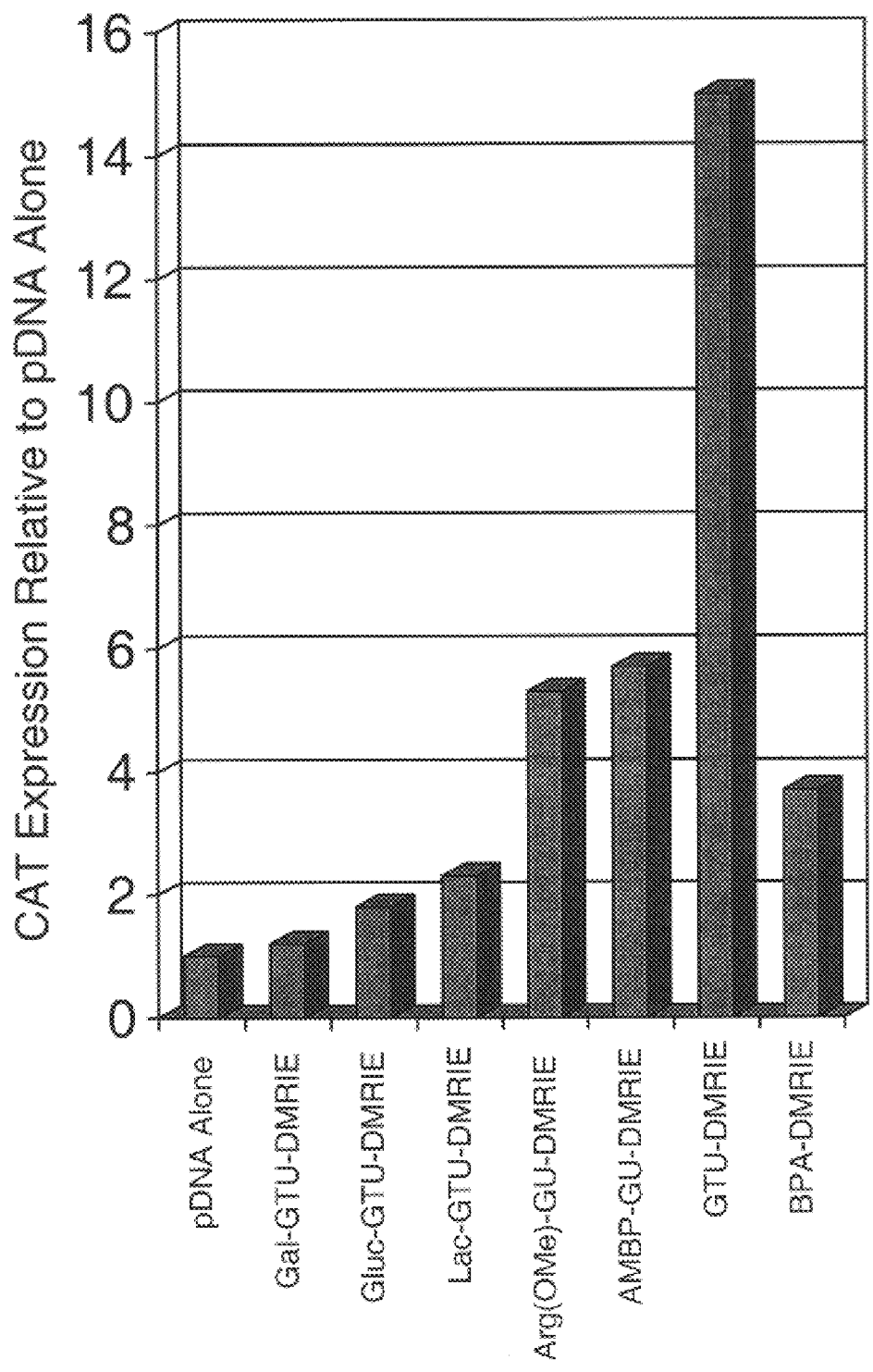
FIG. 7 is a graph of the results of a subcutaneous melanoma assay comparing the activities of Gal-GTU-DMRIE, Glu1-GTU-DMRIE, Lac-GTU-DMRIE, Arg (OMe)-GU-DMRIE, GTU-DMRIE, and BPA-DMRIE to that of DNA alone.

The results are summarized in FIG. 7. Each of the compounds exibited greater activity than the naked DNA control. Arg(OMe)-GU-DMRIE, AMBP-GU-DMRIE, GTU-DMRIE, and BPA-DMRIE exhibited particularly high activity in this assay.

Without further elaboration, it is believed that one skilled in the art can, using the preceding description, utilize the invention to its fullest extent. The invention may be embodied in other specific forms without departing from its spirit of essential characteristics. The described embodiments are to be considered in all respects only as illustrative and not restrictive, and the scope of the invention is therefore indicated by the appended claims rather than by the foregoing description. All modifications which come within the meaning and range of the lawful equivalency of the claims are to be embraced within their scope.

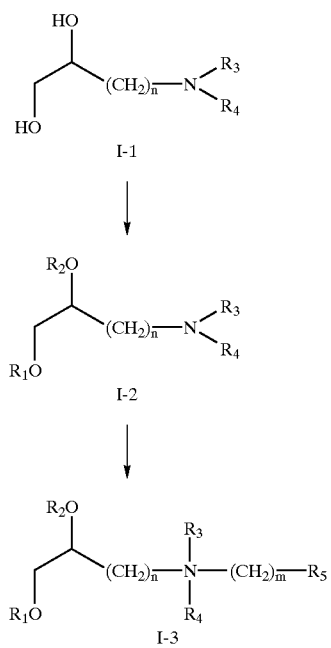

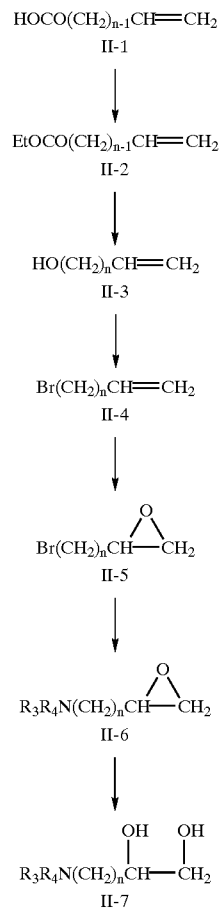

Scheme III
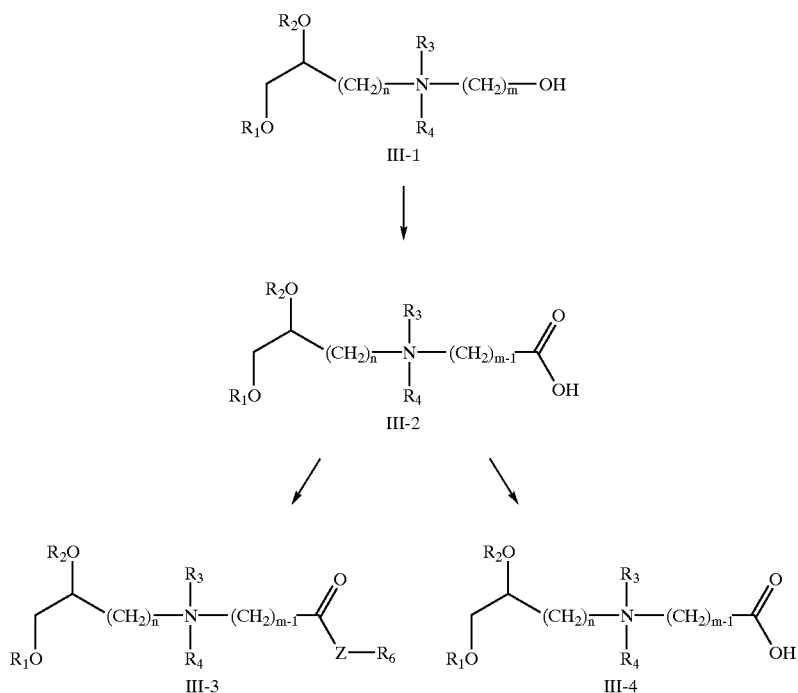
Scheme IV
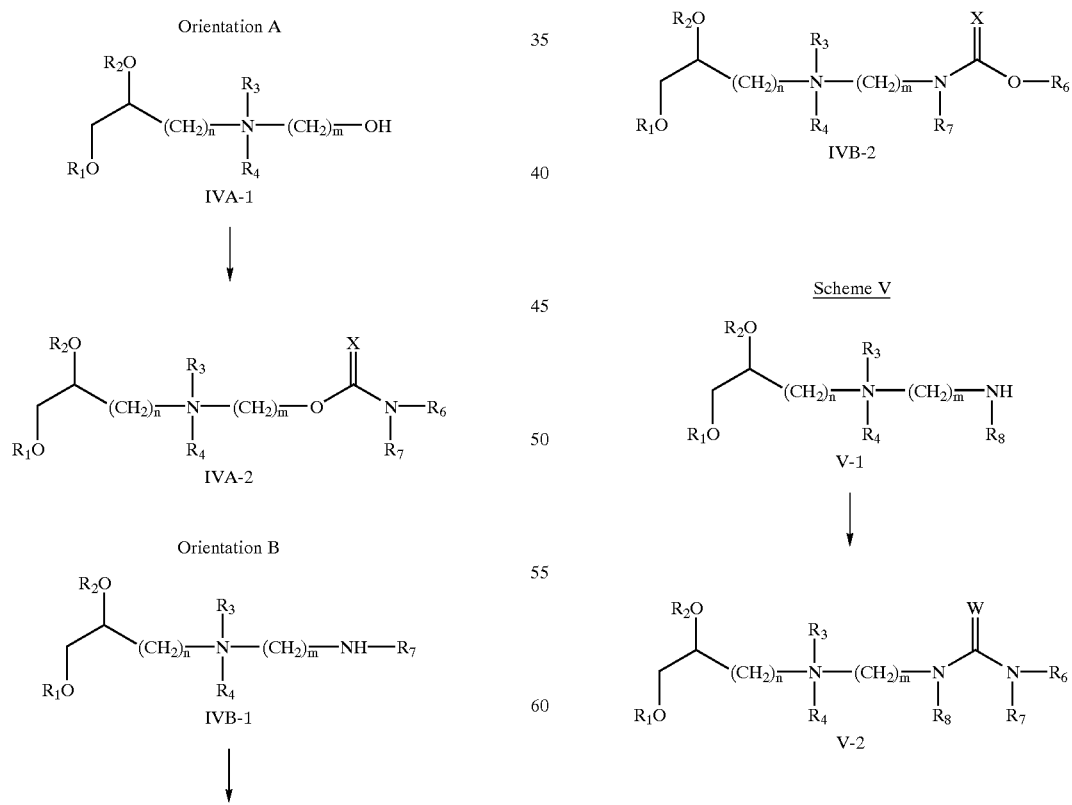

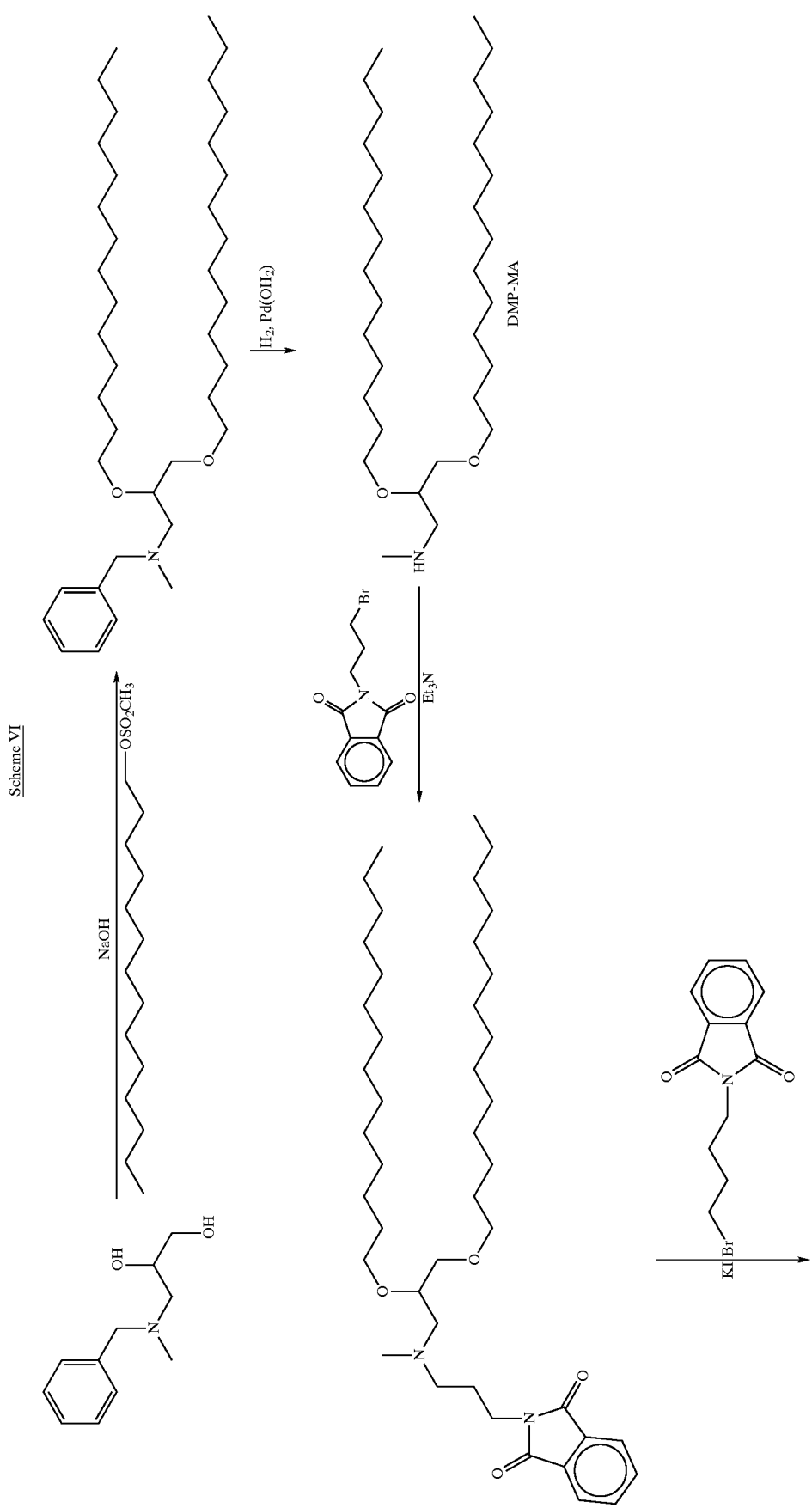

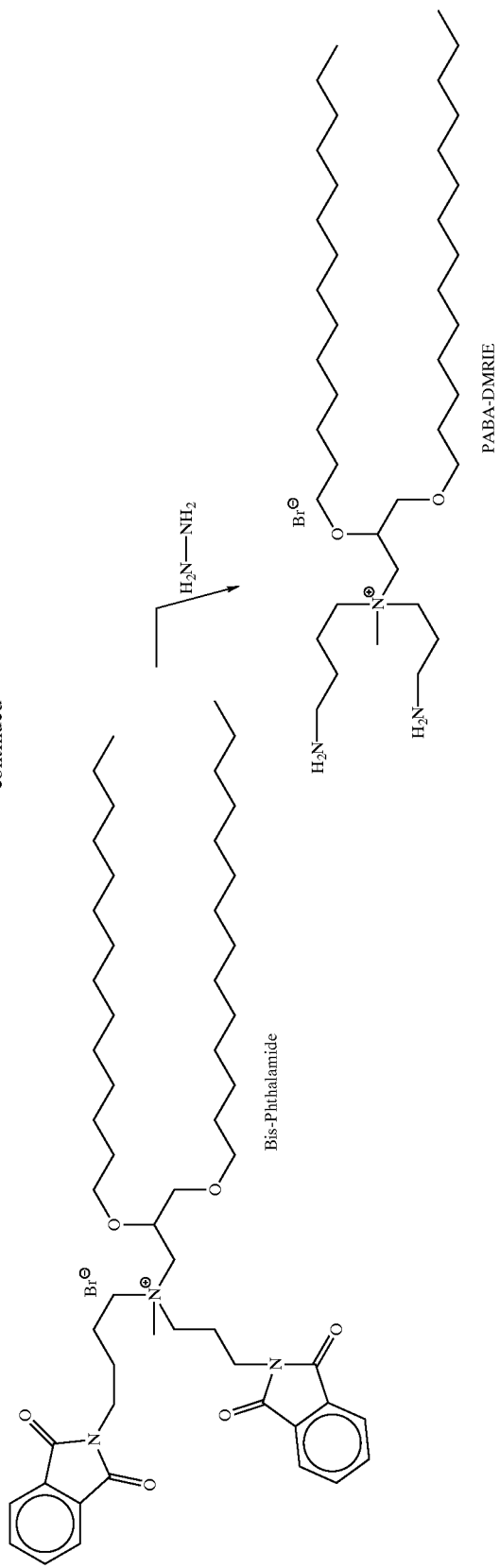

What is claimed is:

1. A compound of the formula:

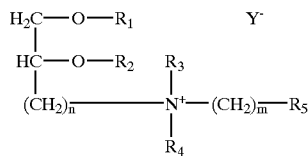

R$_1$ and R$_2$ are independently H; linear or branched, unsubstituted or substituted C$_{1-23}$ alkyl, acyl, alkenyl, or heteroalkyl group having from 0 to 6 sites of unsaturation; or a cyclic or aryl group, said heteroalkyl, cyclic, and aryl groups comprising from 0 to 5 heteroatoms wherein said heteroatoms are not the first atoms in said groups, wherein the substituent groups are selected from the group consisting of —O—(CH$_2$)$_k$—CH$_3$, —S—(CH$_2$)$_k$—CH$_3$, and X—(CH$_2$)$_k$—, wherein X is a halide, and k is 0 to 4;

R$_3$ and R$_4$ are independently H; linear or branched, unsubstituted or substituted C$_{1-23}$ alkyl, acyl, alkenyl, or heteroalkyl group having from 0 to 6 sites of unsaturation; or a cyclic or aryl group, said heteroalkyl, cyclic, and aryl groups comprising from 0 to 5 heteroatoms wherein said heteroatoms are not the first atoms in said groups, wherein the substituent groups are selected from the group consisting of —O—(CH$_2$)$_k$—CH$_3$, —S—(CH$_2$)$_k$—CH$_3$, and X—(CH$_2$)$_k$—, wherein X is a halide, and k is 0 to 4;

R$_5$ has the structure

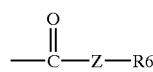

wherein

Z is selected from the group consisting of O, S, NR$_1$, NH, Se, and CR$_7$R$_8$;

R$_6$ is selected from the group consisting of H, R$_1$, R$_2$, R$_3$, and R$_4$, and, when Z is O, NH, NR$_1$, or S, R$_6$ can further be an amino acid, peptide, polypeptide, protein, mono-, di- or polysaccharide, or other bioactive or pharmaceutical agent, wherein Z is an atom of said amino acid, peptide, polypeptide, protein, mono-, di- or polysaccharide, or other bioactive or pharmaceutical agent;

n is 1 to 6;

m is 1 to 10;

Y is a pharmaceutically acceptable anion; and

R$_7$ and R$_8$ independently or in combination are H or alkyl groups as defined for R$_1$ and R$_2$;

wherein if Z is O, n is 1, and m is 3, then R$_6$ is selected from the group defined for R$_3$ and R$_4$ and wherein R$_1$ and R$_2$ are not both H.

2. A compound according to claim 1 wherein R$_1$ and R$_2$ are C$_{10}$ to C$_{20}$ alkyl or alkenyl groups, Z is O and R$_6$ is an amino acid or peptide linked to Z as an ester.

3. A compound according to claim 1, wherein Z is O, R$_1$ and R$_2$ are identical and are selected from the group consisting of C$_{14}$H$_{29}$ and (CH$_2$)$_8$CH=CH(CH$_2$)$_7$CH$_3$, and R$_3$ and R$_4$ are methyl.

4. A compound according to claim 1, wherein R$_1$ and R$_2$ are saturated or unsaturated C$_{10}$–C$_{18}$ alkyl groups.

5. A compound according to claim 1, wherein R$_1$ and R$_2$ are identical and are selected from the group consisting of C$_{14}$H$_{29}$ and C$_{12}$H$_{25}$.

6. A compound according to claim 5, wherein R$_3$ and R$_4$ are selected from the group consisting of C$_1$–C$_5$ alkyl groups and C$_1$–C$_5$ heteroalkyl groups having one heteroatom therein.

7. A compound according to claim 6 wherein R$_3$ and R$_4$ are methyl groups.

8. A compound according to claim 1, wherein R$_6$ is selected from the group consisting of H, R$_1$, R$_2$, R$_3$, and R$_4$.

9. A compound according to claim 1, wherein Z is O.

10. A compound according to claim 1, wherein Z is NH or NR$_1$.

11. A compound according to claim 1, wherein said compound is selected from the group consisting of DORIE carboxylate(dioleyl Rosenthal Inhibitor Ether carboxylate), DMRIE carboxylate(dimyristyl Rosenthal Inhibitor Ether carboxylate), DMRIE carboxylate propyl amide, DMRIE carboxylate(methionine-methylester)amide, DMRIE carboxylate(methionine-leucine-methylester)amide, and DMRIE carboxylate(methionine-leucine-phenylalanine-methylester)amide.

12. A compound of the formula:

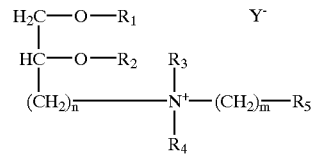

wherein

R$_1$ and R$_2$ are saturated or unsaturated C$_{10}$–C$_{18}$ alkyl groups;

R$_3$ and R$_4$ are independently H; linear or branched, unsubstituted or substituted C$_{1-23}$ alkyl, acyl, alkenyl, or heteroalkyl group having from 0 to 6 sites of unsaturation; or a cyclic or aryl group, said heteroalkyl, cyclic, and aryl groups comprising from 0 to 5 heteroatoms wherein said heteroatoms are not the first atoms in said groups, wherein the substituent groups are selected from the group consisting of —O—(CH$_2$)$_k$—CH$_3$, —S—(CH$_2$)$_k$—CH$_3$, and X—(CH$_2$)$_k$—, wherein X is a halide, and k is 0 to 4;

R$_5$ has the structure:

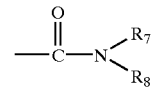

R$_7$ and R$_8$ are independently selected from the group defined for R$_1$, R$_2$, R$_3$ and R$_4$, and one of R$_7$ and R$_8$ can further be an amino acid, peptide, polypeptide, protein, mono-, di- or polysaccharide, or other bioactive or pharmaceutical agent, wherein an amino nitrogen of said amino acid, peptide, polypeptide, protein, mono-, di- or polysaccharide, or other bioactive or pharmaceutical agent is the N to which R$_7$ or R$_8$ is attached;

n is 1 to 6;

m is 1 to 10; and

Y is a pharmaceutically acceptable anion.

13. A compound according to claim 12, wherein R$_1$ and R$_2$ are identical and are selected from the group consisting of C$_{14}$H$_{29}$ and C$_{12}$H$_{25}$.

14. A compound according to claim 13, wherein R$_3$ and R$_4$ are selected from the group consisting of C$_1$–C$_5$ alkyl groups and C$_1$–C$_5$ heteroalkyl groups having one heteroatom therein.

15. A compound according to claim 14, wherein $R_3$ and $R_4$ are methyl groups.

16. A compound according to claim 12, wherein $R_7$ and $R_8$ are independently selected from the group defined for $R_1$, $R_2$, $R_3$ and $R_4$.

17. A compound according to claim 12, wherein $R_1$ and $R_2$ are $C_{10}$ to $C_{20}$ alkyl or alkenyl groups, $R_7$ is H, and $R_8$ is an amino acid or peptide.

18. A compound of the formula:

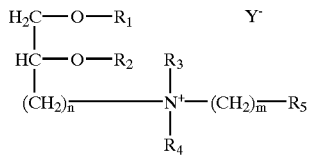

wherein $R_1$ and $R_2$ are saturated or unsaturated $C_{10}$–$C_{18}$ alkyl groups;

$R^3$ and $R^4$ are independently H; linear or branched, unsubstituted or substituted $C_{1-23}$ alkyl, acyl, alkenyl or heteroalkyl group having from 0 to 6 sites of unsaturation; or a cyclic or aryl group, said heteroalkyl, cyclic, and aryl groups comprising from 0 to 5 heteroatoms wherein said heteroatoms are not the first atoms in said groups, wherein the substituent groups are selected from the group consisting of —O—$(CH_2)_k$—$CH_3$, —S—$(CH_2)_k$—$CH_3$, and X—$(CH_2)_k$—, wherein X is a halide, and k is 0 to 4;

wherein $R_5$ has the structure

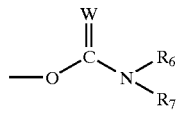

wherein $R_6$ and $R_7$ are independently selected from the group defined for $R_1$, $R_2$, $R_3$ and $R_4$ and one of $R_6$ and $R_7$ can further be an amino acid, peptide, polypeptide, protein, mono-, di- or polysaccharide, or other bioactive or pharmaceutical agent, wherein an amino nitrogen of said amino acid, peptide, polypeptide, protein, mono-, di- or polysaccharide, or other bioactive or pharmaceutical agent is the N to which $R_6$ or $R_7$ is attached;

W is O, $NR_8$, NH, S, or Se;

$R_8$ is an alkyl group as defined for $R_1$ and $R_2$;

n is 1 to 6;

m is 1 to 10; and

Y is a pharmaceutically acceptable anion.

19. A compound according to claim 18, wherein $R_1$ and $R_2$ are identical and are selected from the group consisting of $C_{14}H_{29}$ and $C_{12}H_{25}$.

20. A compound according to claim 19, wherein $R_3$ and $R_4$ are selected from the group consisting of $C_1$–$C_5$ alkyl groups and $C_1$–$C_5$ heteroalkyl groups having one heteroatom therein.

21. A compound according to claim 20 wherein $R_3$ and $R_4$ are methyl groups.

22. A compound of the formula:

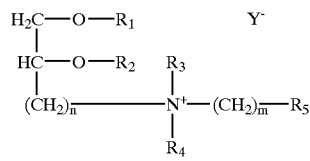

wherein $R_1$ and $R_2$ are saturated or unsaturated $C_{10}$–$C_{18}$ alkyl groups;

$R_3$ and $R_4$ are independently H; linear or branched, unsubstituted or substituted $C_{1-23}$ alkyl, acyl, alkenyl, or heteroalkyl group having from 0 to 6 sites of unsaturation; or a cyclic or aryl group, said heteroalkyl, cyclic, and aryl groups comprising from 0 to 5 heteroatoms wherein said heteroatoms are not the first atoms in said groups, wherein the substituent groups are selected from the group consisting of —O—$(CH_2)_k$—$CH_3$, —S—$(CH_2)_k$—$CH_3$, and X—$(CH_2)_k$—, wherein X is a halide, and k is 0 to 4;

wherein $R_5$ has the structure

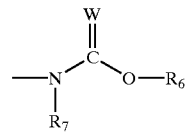

wherein $R_6$ and $R_7$ are independently selected from the group defined for $R_1$, $R_2$, $R_3$ and $R_4$ and one of $R_6$ and $R_7$ can further be an amino acid, peptide, polypeptide, protein, mono-, di- or polysaccharide, or other bioactive or pharmaceutical agent, wherein a hydroxy oxygen of said amino acid, peptide, polypeptide, protein, mono-, di- or polysaccharide, or other bioactive or pharmaceutical agent is the O to which $R_6$ is attached;

W is O, $NR_8$, NH, S, or Se;

$R_8$ is an alkyl group as defined for $R_1$ and $R_2$;

n is 1 to 6;

m is 1 to 10; and

Y is a pharmaceutically acceptable anion.

23. A compound according to claim 22, wherein $R_1$ and $R_2$ are identical and are selected from the group consisting of $C_{14}H_{29}$ and $C_{12}H_{25}$.

24. A compound according to claim 23, wherein $R_3$ and $R_4$ are selected from the group consisting of $C_1$–$C_5$ alkyl groups and $C_1$–$C_5$ heteroalkyl groups having one heteroatom therein.

25. A compound according to claim 24 wherein $R_3$ and $R_4$ are methyl groups.

26. A compound according to claim 18, wherein $R_6$ and $R_7$ are independently selected from the group defined for $R_1$, $R_2$, $R_3$ and $R_4$.

27. A compound according to claim 18, wherein said compound is selected from the group consisting of DMRIE methyl carbamate(dioleyl Rosenthal Inhibitor Ether methyl carbamate), hydroxypropyl DMRIE methyl carbamate, and hydroxybutyl DMRIE methyl carbamate.

* * * * *